(12) United States Patent
Stevenson et al.

(10) Patent No.: US 9,431,814 B2
(45) Date of Patent: Aug. 30, 2016

(54) FERRULE FOR IMPLANTABLE MEDICAL DEVICE

(71) Applicant: Cardiac Pacemakers, Inc., St. Paul, MN (US)

(72) Inventors: Mark Stevenson, Maplewood, MN (US); Meherdil D. Dastur, Saint Paul, MN (US); James Blilie, Shoreview, MN (US); Gregory J. Sherwood, North Oaks, MN (US); Patrick J. Barry, North St. Paul, MN (US); Derek John Boettger, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 286 days.

(21) Appl. No.: 13/765,350

(22) Filed: Feb. 12, 2013

(65) Prior Publication Data

US 2013/0206472 A1    Aug. 15, 2013

Related U.S. Application Data

(60) Provisional application No. 61/682,466, filed on Aug. 13, 2012, provisional application No. 61/598,961, filed on Feb. 15, 2012.

(51) Int. Cl.
| | |
|---|---|
| *H02G 3/18* | (2006.01) |
| *H01J 5/00* | (2006.01) |
| *H01J 15/00* | (2006.01) |
| *H05K 5/06* | (2006.01) |
| *H01G 4/35* | (2006.01) |
| *H01G 4/228* | (2006.01) |

(Continued)

(52) U.S. Cl.
CPC .......... *H02G 15/013* (2013.01); *A61N 1/3754* (2013.01)

(58) Field of Classification Search
CPC ... A61N 1/3754; H01L 23/045; H01R 4/643
USPC .......... 174/50.56, 50.61, 650, 659; 361/302, 361/306.1
See application file for complete search history.

(56) References Cited

U.S. PATENT DOCUMENTS

| | | | | |
|---|---|---|---|---|
| 1,773,811 A | * | 8/1930 | Flachbarth | ..................... 174/486 |
| 2,576,063 A | | 11/1951 | Berta | |
| 3,664,924 A | | 5/1972 | Krawiec | |

(Continued)

FOREIGN PATENT DOCUMENTS

| | | |
|---|---|---|
| EP | 0332763 B1 | 9/1993 |
| GB | 907520 A | 10/1962 |

(Continued)

OTHER PUBLICATIONS

Definition of "tab" from www.merriam-webster.com Jan. 15, 2015.*

(Continued)

*Primary Examiner* — Chau N Nguyen
*Assistant Examiner* — Roshn Varghese
(74) *Attorney, Agent, or Firm* — Schwegman Lundberg & Woessner, P.A.

(57) ABSTRACT

A ferrule for an implantable medical device (IMD) can employ stamped metal portion including an electrically-conductive ferrule portion. The stamped ferrule portion can be affixed to a wall of a housing of the IMD. The resulting ferrule can provide cost savings or higher production throughput over a ferrule employing machined ferrule portion.

19 Claims, 23 Drawing Sheets

(51) Int. Cl.
*H02G 15/013* (2006.01)
*A61N 1/375* (2006.01)

(56) References Cited

U.S. PATENT DOCUMENTS

| | | | |
|---|---|---|---|
| 3,858,151 A * | 12/1974 | Paskert | 174/51 |
| 4,456,786 A * | 6/1984 | Kyle | 174/152 GM |
| 4,858,938 A | 8/1989 | Terwilliger et al. | |
| 4,880,387 A * | 11/1989 | Stikeleather et al. | 174/653 |
| 4,909,085 A | 3/1990 | Hardy et al. | |
| 4,934,366 A | 6/1990 | Truex et al. | |
| 4,940,858 A | 7/1990 | Taylor et al. | |
| 5,175,067 A | 12/1992 | Taylor et al. | |
| 5,306,581 A | 4/1994 | Taylor et al. | |
| 5,333,095 A | 7/1994 | Stevenson et al. | |
| 5,406,444 A | 4/1995 | Selfried et al. | |
| 5,531,003 A | 7/1996 | Seifried et al. | |
| 5,535,097 A | 7/1996 | Ruben et al. | |
| 5,643,694 A | 7/1997 | Heller, Jr. | |
| 5,650,759 A | 7/1997 | Hittman et al. | |
| 5,735,884 A | 4/1998 | Thompson et al. | |
| 5,759,197 A | 6/1998 | Sawchuk et al. | |
| 5,811,206 A | 9/1998 | Sunderland et al. | |
| 5,817,984 A | 10/1998 | Taylor et al. | |
| 5,821,011 A | 10/1998 | Taylor et al. | |
| 5,836,992 A | 11/1998 | Thompson et al. | |
| 5,866,851 A | 2/1999 | Taylor et al. | |
| 5,867,361 A | 2/1999 | Wolf et al. | |
| 5,870,272 A | 2/1999 | Seifried et al. | |
| 5,871,513 A | 2/1999 | Taylor et al. | |
| 5,896,267 A | 4/1999 | Hittman et al. | |
| 5,902,326 A | 5/1999 | Lessar et al. | |
| 5,905,627 A | 5/1999 | Brendel et al. | |
| 5,959,829 A | 9/1999 | Stevenson et al. | |
| 5,973,906 A | 10/1999 | Stevenson et al. | |
| 5,999,398 A | 12/1999 | Maki et al. | |
| 6,008,980 A | 12/1999 | Stevenson et al. | |
| 6,031,710 A | 2/2000 | Wolf et al. | |
| 6,052,623 A | 4/2000 | Fenner et al. | |
| 6,076,017 A | 6/2000 | Taylor et al. | |
| 6,090,503 A | 7/2000 | Taylor et al. | |
| 6,141,205 A | 10/2000 | Nutzman et al. | |
| 6,196,856 B1 * | 3/2001 | De Villeroche | 439/248 |
| 6,212,063 B1 | 4/2001 | Johnson et al. | |
| 6,321,114 B1 | 11/2001 | Nutzman et al. | |
| 6,349,025 B1 | 2/2002 | Fraley et al. | |
| 6,414,835 B1 | 7/2002 | Wolf et al. | |
| 6,456,481 B1 | 9/2002 | Stevenson | |
| 6,490,148 B1 | 12/2002 | Allen et al. | |
| 6,519,133 B1 * | 2/2003 | Eck et al. | 361/302 |
| 6,529,103 B1 | 3/2003 | Brendel et al. | |
| 6,566,978 B2 | 5/2003 | Stevenson et al. | |
| 6,567,259 B2 | 5/2003 | Stevenson et al. | |
| 6,610,443 B2 | 8/2003 | Paulot et al. | |
| 6,622,046 B2 | 9/2003 | Fraley et al. | |
| 6,643,903 B2 | 11/2003 | Stevenson et al. | |
| 6,660,116 B2 | 12/2003 | Wolf et al. | |
| 6,765,779 B2 | 7/2004 | Stevenson et al. | |
| 6,765,780 B2 | 7/2004 | Brendel et al. | |
| 6,768,629 B1 | 7/2004 | Allen et al. | |
| 6,812,404 B1 | 11/2004 | Martinez | |
| 6,850,405 B1 | 2/2005 | Mileham et al. | |
| 6,852,925 B2 | 2/2005 | Wolf et al. | |
| 6,855,456 B2 | 2/2005 | Taylor et al. | |
| 6,882,248 B2 | 4/2005 | Stevenson et al. | |
| 6,888,715 B2 | 5/2005 | Stevenson et al. | |
| 6,899,976 B2 | 5/2005 | Larson et al. | |
| 6,903,268 B2 | 6/2005 | Marshall et al. | |
| 6,920,673 B2 | 7/2005 | Allen et al. | |
| 6,935,549 B2 | 8/2005 | Wolf | |
| 6,951,664 B2 | 10/2005 | Marshall et al. | |
| 6,985,347 B2 | 1/2006 | Stevenson et al. | |
| 6,999,818 B2 | 2/2006 | Stevenson et al. | |
| 7,012,192 B2 | 3/2006 | Stevenson et al. | |
| 7,035,076 B1 | 4/2006 | Stevenson | |
| 7,035,077 B2 | 4/2006 | Brendel | |
| 7,046,499 B1 * | 5/2006 | Imani et al. | 174/152 GM |
| 7,060,900 B1 * | 6/2006 | Gretz | 174/652 |
| 7,064,270 B2 | 6/2006 | Marshall et al. | |
| 7,113,387 B2 | 9/2006 | Stevenson et al. | |
| 7,128,765 B2 | 10/2006 | Paulot et al. | |
| 7,145,076 B2 | 12/2006 | Knappen et al. | |
| 7,164,572 B1 | 1/2007 | Burdon et al. | |
| 7,187,535 B1 | 3/2007 | Iyer et al. | |
| 7,199,995 B2 | 4/2007 | Stevenson | |
| 7,210,966 B2 | 5/2007 | Taylor et al. | |
| 7,281,305 B1 | 10/2007 | Iyer et al. | |
| 7,348,097 B2 | 3/2008 | Nielsen et al. | |
| 7,349,618 B2 | 3/2008 | Nielsen et al. | |
| 7,363,090 B2 | 4/2008 | Halperin et al. | |
| 7,391,601 B1 | 6/2008 | Imani | |
| 7,588,461 B2 * | 9/2009 | Tyler | B60L 3/0069 439/607.41 |
| 7,668,597 B2 * | 2/2010 | Engmark et al. | 607/37 |
| 7,736,191 B1 | 6/2010 | Sochor | |
| 7,747,321 B2 | 6/2010 | Fischbach et al. | |
| 7,789,701 B2 * | 9/2010 | Murr | H01R 13/743 439/552 |
| 7,839,620 B2 | 11/2010 | Iyer et al. | |
| 7,842,415 B2 | 11/2010 | Wutz et al. | |
| 2004/0034368 A1 * | 2/2004 | Pless et al. | 606/129 |
| 2004/0260354 A1 | 12/2004 | Nielsen et al. | |
| 2006/0247714 A1 | 11/2006 | Taylor et al. | |
| 2007/0239223 A1 | 10/2007 | Engmark et al. | |
| 2008/0292958 A1 | 11/2008 | Nielsen et al. | |
| 2009/0192578 A1 * | 7/2009 | Biggs | 607/116 |
| 2010/0199872 A1 | 8/2010 | Fink et al. | |
| 2012/0006576 A1 | 1/2012 | Barry et al. | |
| 2013/0127567 A1 * | 5/2013 | Iyer et al. | 29/852 |

FOREIGN PATENT DOCUMENTS

| | | |
|---|---|---|
| JP | 2002263201 A | 9/2002 |
| JP | 2005040585 A | 2/2005 |
| JP | 2011517970 A | 6/2011 |
| JP | 2012090732 A | 5/2012 |
| JP | 2015509394 A | 3/2015 |
| WO | WO-2009045772 A1 | 4/2009 |
| WO | WO-2013122947 A2 | 8/2013 |
| WO | WO-2013122947 A3 | 8/2013 |

OTHER PUBLICATIONS

"International Application Serial No. PCT/US2013/025762, International Preliminary Report on Patentability rnailed Aug. 28, 2014", 8 pgs.

"International Application Serial No. PCT/US2013/025762, International Search Report mailed Aug. 21, 2013", 3 pgs.

"International Application Serial No. PCT/US2013/025762, Written Opinion mailed Aug. 21, 2013", 6 pgs.

"Japanese Application Serial No. 2014-557724, Office Action mailed Aug. 4, 2015", With English Translation, 5 pgs.

* cited by examiner

FERRULE FOR IMPLANTABLE MEDICAL DEVICE

CLAIM OF PRIORITY

This application claims the benefit of priority under 35 USC 119(e) to U.S. Provisional Application No. 61/598,961, filed on Feb. 15, 2012, entitled, "CAPACITIVE FILTER FERRULE FOR IMPLANTABLE MEDICAL DEVICE," and U.S. Provisional Application No. 61/682,466, filed on Aug. 13, 2012, entitled "FERRULE FOR IMPLANTABLE MEDICAL DEVICE," each of which is incorporated herein by reference in its entirety.

BACKGROUND

An electrical feedthrough can be used in an implantable medical device (IMD) to provide an isolated electrical circuit path from the exterior of the IMD to an interior of a housing. Feedthroughs can be used with housings that are sealed, such as a biocompatible hermetically sealed housing. The electrical path can provide an electrical connection to components inside the housing from outside the housing. To preserve internal components, the feedthrough can be leak-resistant. Some feedthrough designs are biocompatible and hermetically sealed. Some implantable medical devices using such a hermetically sealed housing can protect implanted electronics from body fluids and can resist undesirable exposure of the patient to materials from inside the housing.

To provide such a feedthrough, a ferrule, or mechanical element can be disposed through the housing and coupled to the housing. An electrical conductor can extend through the ferrule. A seal and/or electrical insulator can be disposed between the ferrule and the conductor. A hermetically sealed ferrule configured as such can maintain hermeticity of the case while allowing an electrical signal to enter the case.

A feedthrough connector for an implantable medical device is discussed in U.S. Pat. No. 4,934,366 entitled, "Feedthrough Connector for an Implantable Medical Device." An implantable connector that electrically connects multi-conductor leads to an implantable medical device is discussed in U.S. Pat. No. 7,736,191 entitled, "Implantable Connector with Protected Contacts."

A hermetic implantable medical device is discussed in U.S. Patent No. US 2,006,247,714 entitled, "Glass-to-metal Feedthrough Seals Having Improved Durability Particularly Under AC or DC Bias."

An optical window assembly for use in implantable medical device is discussed in U.S. Pat. No. 5,902,326 entitled, "Optical Window for Implantable Medical Devices."

These approaches have a number of shortcomings, including, but not limited to, complexity, difficulty to manufacture, and high cost.

OVERVIEW

A ferrule can be machined from solid titanium, which can be expensive to manufacture. There is a need for improved techniques of ferrule components such as to lower the cost or increase production throughput.

By way of example, this document describes housing, such as a housing for an implantable medical device, which can include a ferrule that can be configured at least partially within a first passage through the housing, which can provide for passage of an electrical connection, such as a signal, through the ferrule. The signal can be filtered by one or more components coupled to the ferrule, such as capacitors. The housing can include an interior portion, an exterior portion, and a first passage between the interior and exterior portions. The ferrule can include an outer ferrule portion oriented toward an exterior portion of the housing. The outer ferrule portion can optionally be electrically conductive. The ferrule can include an inner ferrule portion oriented toward the interior portion of the housing. The inner ferrule portion can optionally be electrically conductive. The inner ferrule portion can be formed non-integrally, or discretely from, the outer ferrule portion, and can be attached to the outer ferrule portion. The housing can be configured to carry and hermetically enclose an electronic circuit. A dielectric insert that can isolate a ferrule from electrical communication with the housing.

A method can include forming an outer ferrule portion sized or shaped or otherwise configured to fit into a passage between the interior and exterior portions of a housing of an implantable medical device. The outer ferrule portion can be disposed proximal the exterior portion of the housing. The method can include forming an inner ferrule portion sized or shaped or otherwise configured to fit into a passage between an interior and exterior portion of the housing of the implantable medical device. The inner ferrule portion can be disposed proximal the interior portion of the housing. The method can include attaching the outer ferrule portion to the inner ferrule portion. The method can include providing a dielectric insert disposed at least partially inside the passage. The method can include providing an electrical conductor through the dielectric insert, such as through the passage.

Forming the outer ferrule portion can include stamping a sheet such as a web. In an example, a first stamped web carries a plurality of the outer ferrule portions. Forming an inner ferrule portion can also include stamping a sheet such as a web. In an example, a second stamped web carries a plurality of inner ferrule portions. Forming the ferrule can include attaching the outer ferrule portion to the inner ferrule portion, such as by joining the first web with the second web during a roll-to-roll process. In an example, a plurality of outer ferrule portions can be attached to the first web and a plurality of inner ferrule portions can still be attached to the second web. The two webs can be attached in a roll-to-roll process resulting in a plurality of assembled ferrules, each including an inner ferrule fixed to an outer ferrule.

In an example, a dielectric insert can be provided for mating to one or both the inner and outer ferrule such as to provide insulation between various portions of the outer ferrule or the inner ferrule. In some examples, the insert can be provided as part of a process such as a reel-to-reel manufacturing process. Providing the dielectric insert can include providing a plurality of dielectric inserts while the first web is positioned with respect to the second web. For example, the plurality of outer ferrule portions can be attached to the first web, and the plurality of inner ferrule portions can be attached to the second web, while a third web, with dielectric inserts, is positioned, such as between them, to dispose the dielectric insert in the ferrule.

Some examples include providing an electrical conductor through the dielectric insert to provide a conductive path through the ferrule in electrical isolation from one or both of the inner ferrule portion and the outer ferrule portion. In an example, providing the electrical conductor through the dielectric insert can include providing a plurality of electric conductors through respective dielectric inserts while the plurality of outer ferrule portions are attached to the first web and the plurality of inner ferrule portions are attached to the second web.

In an example, a method can include separating individual attached outer and inner ferrule portions from the first and second webs, respectively. A method can include disposing an connected outer and inner ferrule portion within a first passage of a housing of an implantable medical device.

A portion of a ferrule, such as the inner ferrule portion, can include one or more biases, such as spring biases or spring fingers, which can be interference fit against an interior wall of the housing of the implantable medical device. Such a spring bias can draw the outer ferrule portion toward an exterior of the housing of the implantable medical device. It can be useful to hold the ferrule in place while the ferrule is being attached and/or sealed to the housing.

Some examples include a one-piece ferrule. The inner portion and outer portion of the above referenced approach can be formed of the same continuous or monolithic material. The one-piece ferrule can be located at least partially within a passage such as a passage that extends from the interior and exterior of the apparatus or the implantable medical device housing to the exterior. The ferrule can include an exterior flange leading into a tunnel that opens to an interior of the housing. The ferrule can include one or more interior tabs extending away from an interior of the tunnel, an electrically insulative insert disposed at least partially inside the tunnel and a hermetic seal disposed between the electrically insulative insert and the tunnel. The exterior flange can be configured to abut an exterior surface of the metallic housing. The exterior flange can define an exit opening. The tunnel can define a tunnel interior extending away from the exit opening and terminating at the inlet opening of the ferrule. The at least one interior tab can be configured to exert a bias against the metallic housing while the exterior flange abuts the metallic housing.

A method can include stamping a sheet to define a flange and a tunnel extending away from the flange. The method can include cutting the tunnel to define at least one tab. The method can include bending the tab away from the tunnel toward a perimeter of the flange. The method can include excising an inner opening from the tunnel. The inner opening can be in communication with an opening around which the flange extends. The method can include inserting an electrically insulative insert in the tunnel. The method can include disposing a conductor through the electrically insulative insert. The method can include sealing the electrically insulative insert to the conductor. The method can include sealing the electrically insulative insert to the ferrule.

An advantage of ferrules described herein is that they can be provided into two separate portions (i.e., the outer and inner ferrule portions), each of which can be manufactured by stamping. The stamped outer and inner ferrule portions can remain on webs to aid in the manufacturing process. Such a process can provide increased production throughput by using webs, and potentially, a reel-to-reel process can be used to input one or more webs and output finished ferrules.

Another advantage of the ferrules described herein is that they can provide for lower component cost versus machining approaches, which can significantly lower expenses for manufacturers.

Another advantage of ferrules described herein is that they can assist in welding a ferrule to the implantable medical device housing.

Some ferrules described herein can be formed as one-piece ferrules, such as by stamping. Such a one-piece ferrule can be made using a progressive stamping process, which can yield high throughput with lower cost.

Another advantage of the ferrules disclosed herein is that they can provide a hermetic seal for the device with an electrical conductor passing therethrough.

Another advantage of ferrules described herein is that they can hold case halves together. Further, examples having a flange can material weldable to case halves. Some designs, when joined with a housing, provide a cavity for ceramic to be disposed in and gold braze to flow into.

BRIEF DESCRIPTION OF THE FIGURES

The drawings illustrate generally, by way of an example, but not by a way of limitation, various embodiments discussed in the present document.

DETAILED DESCRIPTION

Figure 1:
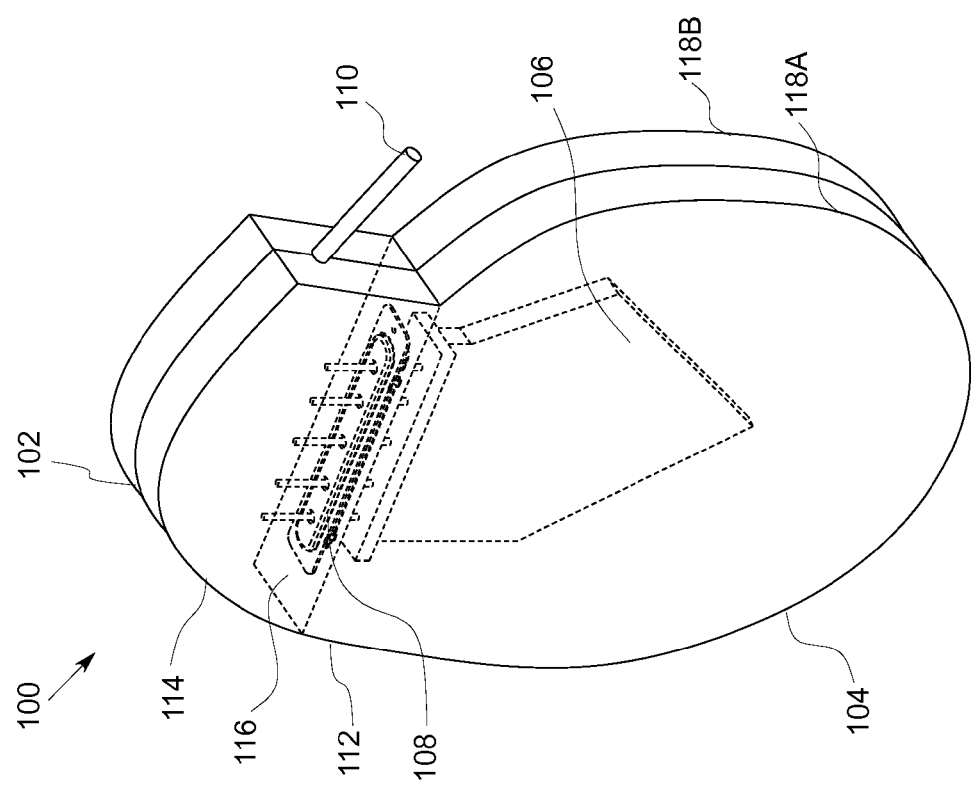
FIG. 1 is a schematic cutaway view diagram of an IMD incorporating a ferrule, according to an example.

FIG. 1 is a schematic cutaway view diagram illustrating generally, by way of an example, but not by way of limitation, an implantable medical device ("IMD") 100 incorporating a ferrule 108 such as a capacitive filter ferrule. The IMD 100 can include a header 102, a housing 104, and one or more electronic circuits such as a printed circuit board (PCB) or a hybrid circuit (e.g., one formed at least in part of flex-circuit) or other circuit 106. The hybrid circuit 106 can be a miniaturized electronic circuit manufactured of individual devices, such as semiconductor devices (e.g. transistors and diodes) and passive components (e.g. resistors, inductors, transformers, and capacitors), attached to a substrate or printed circuit board (PCB).

The header 102 can be coupled to one or more other implantable components, such as a lead 110. The IMD 100 can be operated with one or more leads such as the lead 110 such as, for example, for conveying cardiac electrostimulation or neurostimulation, or impedance or other conductivity characteristic measurement test energy from the IMD 100, or for conveying one or more electric cardiac or other signals from the heart to a sensing circuitry of the IMD 100. The housing 104 can include an interior portion 112, an exterior portion 114, and a first passage 116 between the interior 112 and exterior 114 portions, respectively, of the housing 104. The circuit 106 can be disposed within a hermetically-sealed interior portion 112 of the housing 104. The ferrule 108 can be affixed or otherwise coupled to the housing 104, and can extend partially within the first passage 116 (between the interior and exterior portions 112 and 114, respectively, of the housing 104) such as to allow capacitively-filtered or other passage of an electrical current via an electrical conductor.

Figure 2:
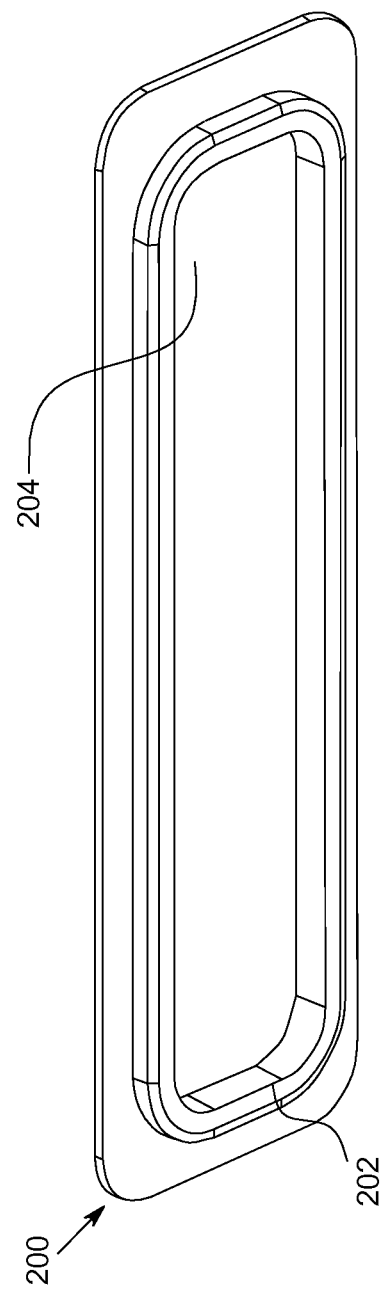
FIG. 2 is a perspective view diagram of an outer ferrule portion, according to an example.
Figure 3:
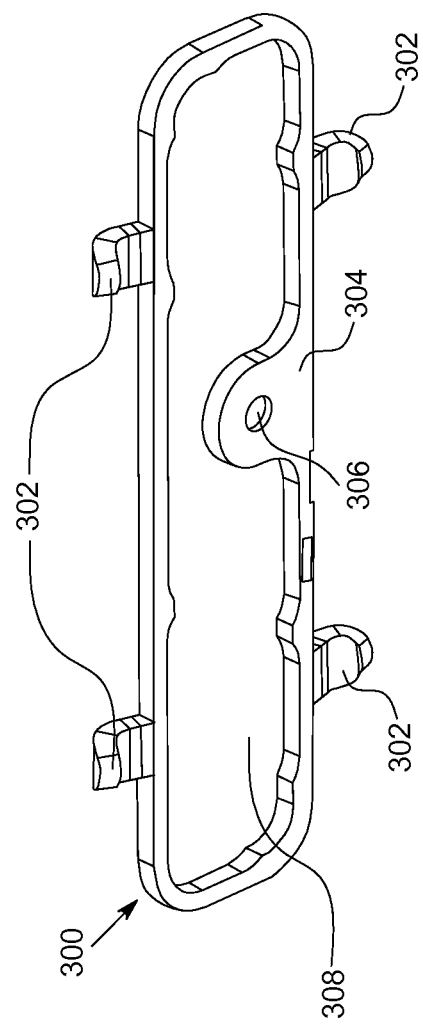
FIG. 3 is a perspective view diagram of an inner ferrule portion, according to an example.

In an example, the ferrule 108 can be a one-piece ferrule as illustrated in FIG. 13. In an example, the ferrule 108 can be a two piece ferrule 108' as illustrated in FIGS. 2-3. An IMD 100 can include a header 102 that can enclose a portion of the ferrule 108' extending out of the housing 104. The header 102 can couple a terminal block on a proximal end of the lead 110 to a circuit 106 via the ferrule 108'.

A circuit 106 can electrically couple to the portion of the ferrule 108' that extends within the interior portion 112 of the housing 104. During operation of the IMD 100, the circuit 106 can communicate with an electrode at the distal end of the lead 110 by way of the ferrule 108'. The housing 104 of the IMD 100 can include or can be formed of a biocompatible material, such as titanium. In an example, one or more biocompatible materials, such as niobium, platinum, or one or more other biocompatible materials can be used.

Referring now to FIGS. 2 and 3, the two portions of the two piece ferrule are described. FIG. 2 is a perspective view diagram illustrating generally, by way of an example, but not by way of limitation, an outer ferrule portion 200. In an example, the outer ferrule portion 200 can be electrically-conductive. The outer ferrule portion 200 can be stamped from a suitable material, such as sheet metal, or can be formed in another way. The outer ferrule portion 200 can include or can be composed of an electrically-conductive biocompatible material, such as titanium. One or more other materials such as one or more of niobium, niobium-titanium alloy, titanium-6Al-4V alloy, platinum, iridium, molybdenum, zirconium, tantalum, vanadium, tungsten, palladium, nickel super alloy, alloys, mixtures, and/or one or more combinations thereof can be used for manufacturing the outer ferrule portion 200. The outer ferrule portion 200 can be shaped like a rectangular frame defining a rectangular opening 204, or can have another shape. Although not a requirement, the outer ferrule portion 200 can be made of a biocompatible material, such as the same material as the housing 104 of the IMD 100, such as for facilitating attachment to the exterior portion 114 of the housing 104. The outer ferrule portion 200 can include a drawn or extruded or otherwise formed seat portion 202 sized or shaped or otherwise configured to fit within a passage such as first passage 116. A snug fit can be provided, which can help form a hermetic seal between the seat portion 202 and the first passage 116 of the housing 104. The snug fit can permit welding or brazing the electrically-conductive outer ferrule portion 200 to the exterior portion 114 of the housing 104.

FIG. 3 is a perspective view diagram illustrating generally, by way of an example, but not by way of limitation, an inner ferrule portion 300. The inner ferrule portion 300 can be stamped from a suitable material, such as sheet metal, or can be formed in another way. The inner ferrule portion 300 can include or can be composed of an electrically-conductive material, such as titanium. One or more other materials such as one or more of niobium, niobium-titanium alloy, titanium-6Al-4V alloy, platinum, iridium, molybdenum, zirconium, tantalum, vanadium, tungsten, palladium, nickel super alloy, or one or more alloys, mixtures, or combinations thereof can be used for manufacturing the inner ferrule portion 300. The inner ferrule portion 300 can be shaped like a rectangular frame. The inner ferrule portion 300 can be similar to the shape of the outer ferrule portion 200. The length of the inner ferrule portion 300 and the length of the outer ferrule portion 200 can be the same or different. The width of the outer ferrule portion 200 can exceed the width of the inner ferrule portion 300. The width of the outer ferrule portion 200 can be less than the width of the inner ferrule portion 300. The inner ferrule portion 300 can be made of a biocompatible material or of one or more non-biocompatible materials, such as to reduce the manufacturing cost.

The inner ferrule portion 300 can include at least one member or tab such as an elastically flex tab 302 that can extend outward, away from an inner ferrule portion opening 308. The flex tab 302 can be made of a flexible or resilient material that can be flexed (e.g., inelastically deformed to assume and retain a new shape) upward or away from a frame of the inner ferrule portion 300 during the stamping process. FIG. 3 depicts an example in which the inner ferrule portion 300 can include four flex tabs similar to the flex tab 302, but more or a fewer flex tabs 302 can be used. The inner ferrule portion 300 and the outer ferrule portion 200 can be two separate portions that can be attached to each other, or each can be attached to the housing 104. The outer ferrule portion 200 can be attached to the inner ferrule portion 300. The inner ferrule portion 300 can be formed non-integrally with the outer ferrule portion 200, but can be attached to the outer ferrule portion 200. The inner ferrule portion 300 can be electrically-conductive and can include an electrically-conductive tab 304. The electrically-conductive tab 304 can include a second passage 306. The second passage 306 can be sized or shaped for passing an electrical conductor (e.g., as described below in conjunction with FIG. 5). The second passage 306 can permit an electrical connection between the electrical conductor and the electrically-conductive tab 304. The electrical conductor can be made of a material that can include, but is not limited to, one or more of tantalum, niobium, titanium, molybdenum, copper, or one or more alloys of any of these.

Figure 4:
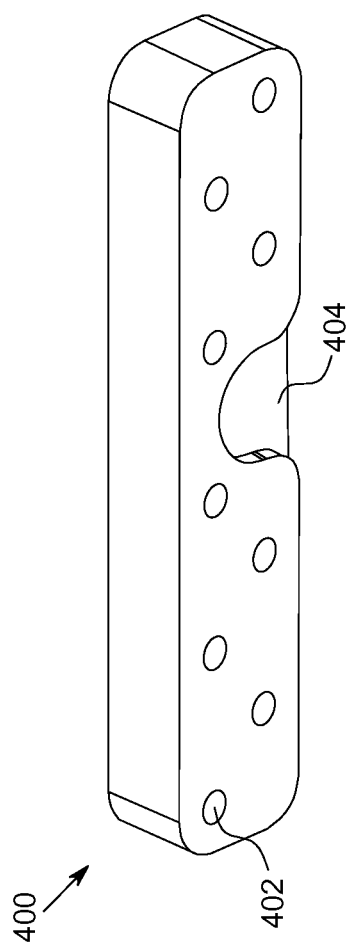
FIG. 4 is a perspective view diagram of a dielectric insert, according to an example.

FIG. 4 is a perspective view diagram illustrating generally, by way of an example, but not by way of limitation, an insert such as a dielectric insert 400. FIG. 4 depicts an example that can include one or a plurality of lumens such as through lumens 402. The lumens 402 can pass the respective electrical conductors. More or a few through lumens 402 or conductors (than that shown in FIG. 4) can be employed. The dielectric insert 400 can be at least partially disposed between and carried within the outer ferrule portion 200 and the inner ferrule portion 300. The dielectric insert 400 can operate to electrically isolate the electrical connection of a conductor passing through the lumens 402 from the electrically-conductive outer ferrule portion 200. The dielectric insert 400 can include a recess 404. The recess 404 can be sized or shaped or otherwise configured to receive a tab such as the electrically-conductive tab 304 of the inner ferrule portion 300. This can permit an electrically-conductive element to pass through the lumens 402 in the electrically-conductive tab 304 and the recess 404. In an example, the dielectric insert 400 can be metallized. Metalizing can be accomplished by sputtering a thin layer of metal such as titanium onto the dielectric insert 400. Other metals can also be used in metalizing. Metalizing the dielectric insert 400 can improve a brazing operation to join the dielectric insert 400 to another component, such as the ferrule 108'.

Conductive portions isolated by the non-conducting dielectric insert 400 can provide a capacitor structure. The capacitive structure can be disposed within the housing 104 and partially disposed within the ferrule 108'. The capacitive structure can be operatively coupled to a distal portion of the conductor. This capacitor can help filter unwanted electromagnetic interference (e.g., EMI) from passing through a feedthrough to which the outer ferrule portion 200 and inner ferrule portion 300 can be coupled. The dielectric insert 400 can include or can be composed of a ceramic material such as the one or more of alumina, co-fired alumina, boron nitride, or another ceramic material.

Figure 5:
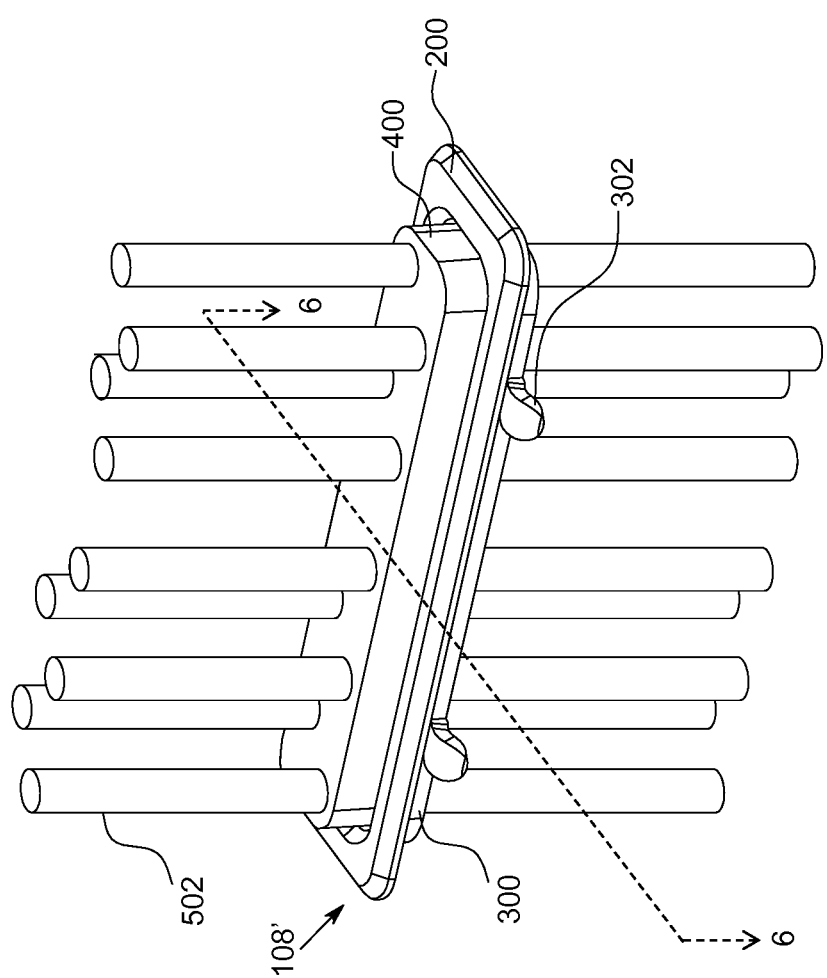
FIG. 5 is a perspective view diagram of a ferrule, according to an example.

FIG. 5 is a perspective view diagram illustrating generally, by way of an example, but not by way of limitation, the ferrule 108'. The ferrule 108' can include an electrically-conductive outer ferrule portion 200, an electrically-conductive inner ferrule portion 300, one or more conductors 502, and a dielectric insert 400, as described herein. The electrically-conductive outer ferrule portion 200 can be configured to be located on the exterior portion 114 of the housing 104. The inner ferrule portion 300 can be configured to be located within the interior portion 112 of the housing 104. The outer ferrule portion 200 can be attached to the inner ferrule portion 300. The outer ferrule portion 200 can be welded or affixed to the inner ferrule portion 300, such as through joining, such as by a laser weld or another coupling. The outer ferrule portion 200 can be vacuum-fused or otherwise affixed to the inner ferrule portion 300. One or more other joining techniques can be employed, such as brazing or another joining technique.

The dielectric insert 400 can be at least partially disposed within a frame provided by the outer ferrule portion 200 and the frame provided by the inner ferrule portion 300. The dielectric insert 400 can be hermetically attached to the one or both of the outer ferrule portion 200 and the inner ferrule portion 300, such as by brazing or welding. The dielectric insert 400 can extend into the interior of the housing. The dielectric insert 400 can extend out of the housing to an exterior region.

The outer ferrule portion 200 can include a stamped sheet metal portion that can be sized or shaped to accept a portion of the dielectric insert 400 within the frame provided by the outer ferrule portion 200. The inner ferrule portion 300 can also include a stamped sheet metal portion that can be sized or shaped to accept a portion of the dielectric insert 400 within the frame provided by the inner ferrule portion 300. The dielectric insert 400 can operate to electrically isolate one or more conductors 502 from the electrically-conductive outer ferrule portion 200.

In the example of FIG. 5, one or more conductors 502 can pass through respective apertures in the dielectric insert 400. The one or more conductors 502 can extend through the dielectric insert 400, which can be disposed within the frame provided by the outer ferrule portion 200 and the inner ferrule portion 300. One or more conductors 502 can be hermetically sealed within respective apertures in the dielectric insert 400, such as by brazing or another technique suitable for providing such a seal.

The ferrule 108' can be configured to be located at least partially within the first passage 116 (between the interior and exterior portions 112 and 114, respectively, of the housing 104). The ferrule 108' can allow for capacitively-filtered or other passage of signals along the one or more conductors 502 between electronics in the housing 104 to electronics or other loads outside and the housing 104.

Figure 6:
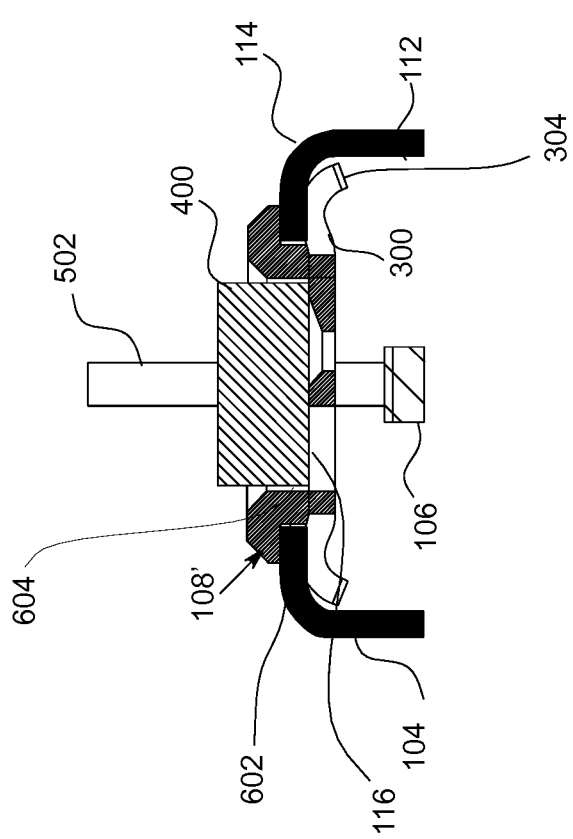
FIG. 6 is a cross-sectional view diagram of FIG. 5 taken along an axis 6-6, according to an example.

FIG. 6 is a cross-sectional view diagram of FIG. 5 taken along an axis 6-6, according to an example. The ferrule 108' can include or can be composed of an electrically-conductive, biocompatible material such as titanium, similar to the material used to construct the housing 104 of the IMD 100. The ferrule 108' can be sized or shaped or otherwise adapted to mate with the interior and exterior portions 112 and 114, respectively, of the housing 104 that can be adjacent to the first passage 116 such as for allowing the capacitively-filtered or other passage of the one or more conductors 502 within the first passage 116. The ferrule 108' can be hermetically attached to the housing 104 such as by welding or brazing or another attachment technique. The electrically-conductive outer ferrule portion 200 can be configured to be hermetically attached or otherwise attached to the exterior portion 114 of the housing 104.

The inner ferrule portion 300 can be configured to exert a bias against a portion of the interior portion 112 of the housing 104. The inner ferrule portion can be disposed adjacent to the first passage 116. The inner ferrule portion 300 can include the flex tab 302 (e.g., as discussed with respect to FIG. 2B) that can be configured to be bent toward the outer ferrule portion 200 such as shown in FIG. 6. The adjacent regions of the interior and exterior portions 112 and 114, respectively, of the housing 104 can be configured to be inserted into a space or slot 602 that can be provided laterally between the coupled outer ferrule portion 200 and the inner ferrule portion 300. Two halves of a clamshell shaped housing can be closed around the ferrule 108', disposed in the slot 602.

Adjacent portions of the housing 104 can exert a force on the flex tab 302 of the inner ferrule portion 300. This can enable the flex tab 302 of the inner ferrule portion 300 to flex to generate a biasing force against the portions of the housing 104 of the IMD 100, such as to draw the outer ferrule portion 200 toward or against the exterior portion 114 of the housing 104. This can be helpful in holding the ferrule in place. The biasing force can aid in holding the outer ferrule portion 200 flush against the exterior portion 114 of the housing 104 and can help secure the ferrule 108' such as during welding or otherwise affixing of the outer ferrule portion 200 to the housing 104 of the IMD 100. After such welding or other hermetically-sealing affixation of the outer ferrule portion 200 to the housing 104, the flex tab 302 may straighten such as to extend laterally outward due to the biasing force.

The dielectric insert 400 can be partially disposed within a peripheral frame 604 provided by the outer ferrule portion 200 and the inner ferrule portion 300, respectively, and can be hermetically attached to the outer ferrule portion 200 and the inner ferrule portion 300, respectively. The dielectric insert 400 can be further configured to fit within a lateral peripheral dimension of the first passage 116 between the interior and exterior portions 112 and 114, respectively, of the housing 104.

In this example, the circuit 106 can be adapted to receive or otherwise be electrically connected to the one or more conductors 502. In an example, the conductors 502 can be soldered or welded or otherwise electrically and mechanically connected to a conductive pad or terminal on the circuit 106.

Figure 7:
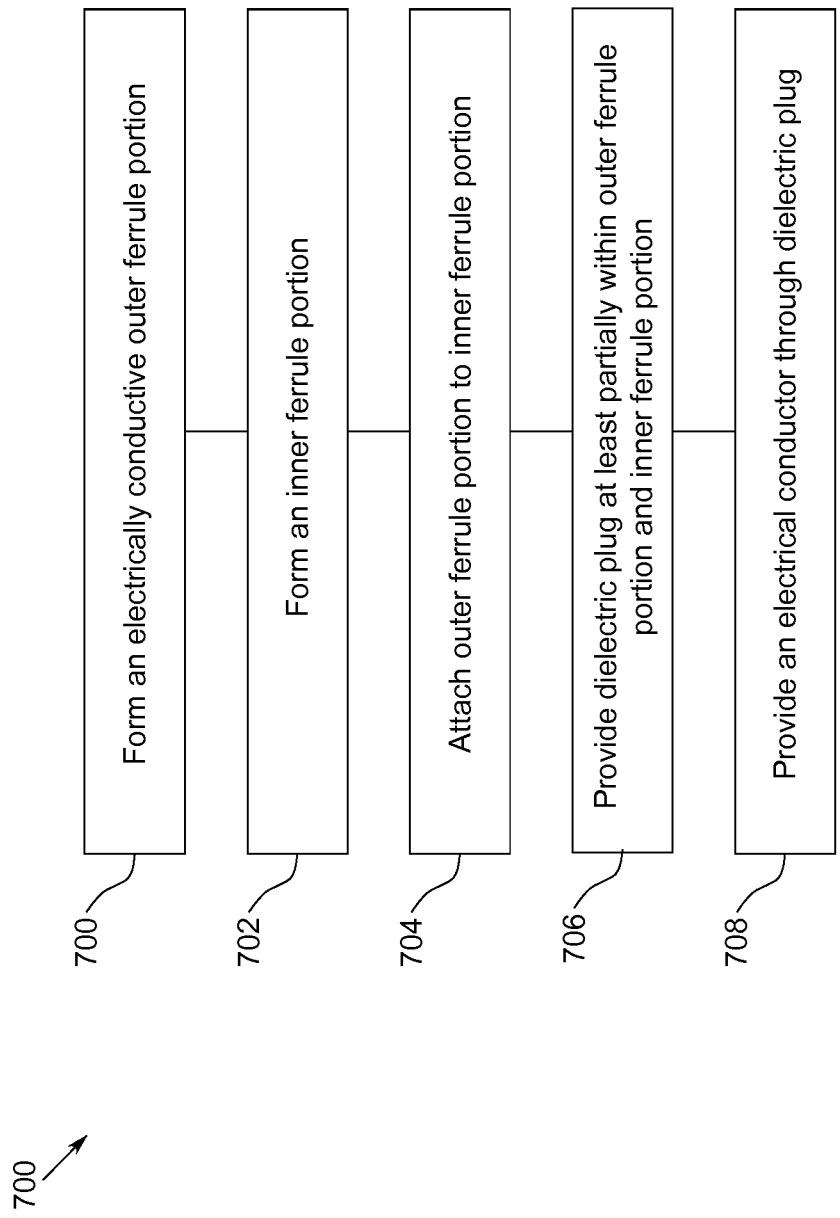
FIG. 7 is a diagram of a method of manufacturing a ferrule, according to an example.

FIG. 7 is a diagram illustrating generally, by way of an example, but not by way of limitation, a method of manufacturing a ferrule such as the ferrule 108'. At 700, an electrically-conductive outer ferrule portion 200 can be formed to include one or more stamped sheet metal portions (e.g., those discussed in conjunction with FIGS. 2, 5, and 6). This can include stamping a titanium or other metal sheet, such as to form the one or more stamped sheet metal portions of the outer ferrule portion 200 for creating a passage through the sheet, which can be stamped to be sized or shaped or otherwise configured to be located toward and welded or brazed to the exterior portion 114 of the housing 104.

At 702, an electrically-conductive inner ferrule portion 300 can be formed, such as to include one or more stamped sheet metal portions (such as discussed in conjunction with FIGS. 3, 5, and 6). This can include stamping a titanium or other metal sheet, such as to form the one or more stamped sheet metal portions of the inner ferrule portion 300 for creating a passage through the sheet, which can be stamped to be sized or shaped or otherwise configured to be attached and sealed at the interior portion 112 of the housing 104, such as by welding or brazing. At 702, the stamping of the inner ferrule portion 300 can include or can be accompanied by stamping the metal sheet to form a flex tab 302 (such as discussed above), such as for extending toward and biasing against a portion of an interior portion 112 of the housing 104.

At 704, the outer ferrule portion 200 and the inner ferrule portion 300 can be attached. In an example, the outer ferrule portion 200 can be attached to the inner ferrule portion 300 by a laser weld or other welding or attachment technique. In an example, the outer ferrule portion 200 can be vacuum-fused or otherwise attached to the inner ferrule portion 300. In an example, one or more other attachment techniques, such as brazing or any other attachment technique can be used.

At 706, a dielectric insert 400 can be provided such that the dielectric insert 400 is captured partially within the lateral peripheral frame provided by the outer 200 and the inner ferrule portion 300 (such as discussed above in FIGS. 4 and 5).

At 708, one or more conductors 502 can be provided through the dielectric insert 400. One or more conductors 502 can pass through a respective aperture in the dielectric insert 400. The conductors 502 that are located within a respective aperture through the dielectric insert 400 can be hermetically sealed within aperture in the dielectric insert 400 such as by brazing or another technique suitable for such sealing. The one or more conductors 502 can extend through the dielectric insert 400, which can be disposed within the frame provided by the outer ferrule portion 200 and the inner ferrule portion 300 (such as discussed above in FIGS. 4 and 5). An electrically-conductive outer ferrule portion 200 can be formed to include one or more stamped sheet metal portions (such as discussed in conjunction with FIGS. 2, 5, and 6)

The above described order of steps of the method is an example. The method can be performed in a different sequence of steps other than that described above. For example, the one or more conductors 502 can first be provided through the dielectric insert 400. The method then can include providing the electrically-conductive outer ferrule portion 200 and the electrically-conductive inner ferrule portion 300. The method can further include attaching the outer ferrule portion 200 and the inner ferrule portion 300. Then, the dielectric insert 400 can be captured partially within the lateral peripheral frame provided by the outer ferrule portion 200 and the inner ferrule portion 300 (such as discussed above in FIGS. 4 and 5).

Figure 8:
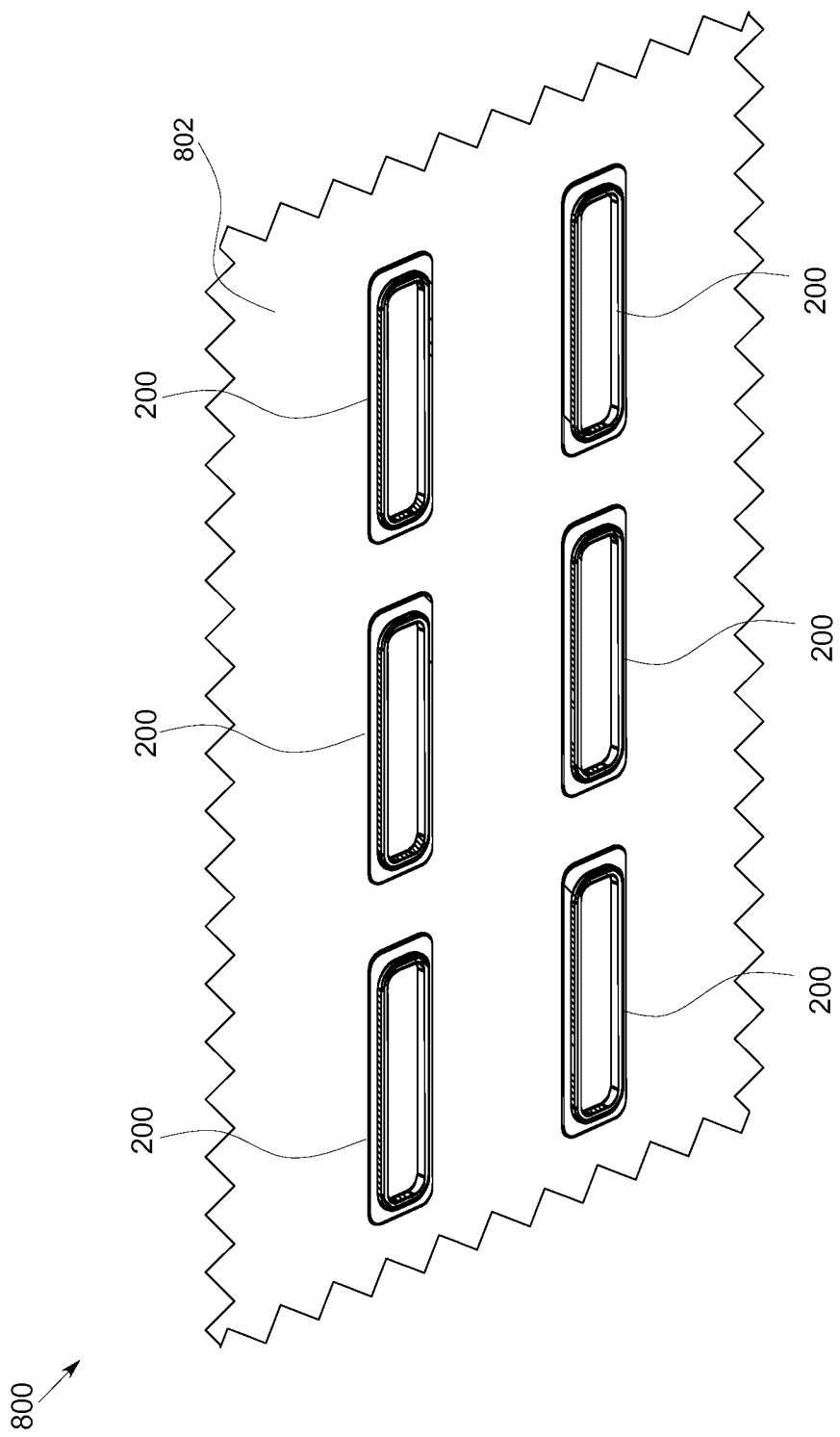
FIG. 8 is a perspective view diagram of multiple outer ferrule portions adhered to a first web, according to an example.
Figure 9:
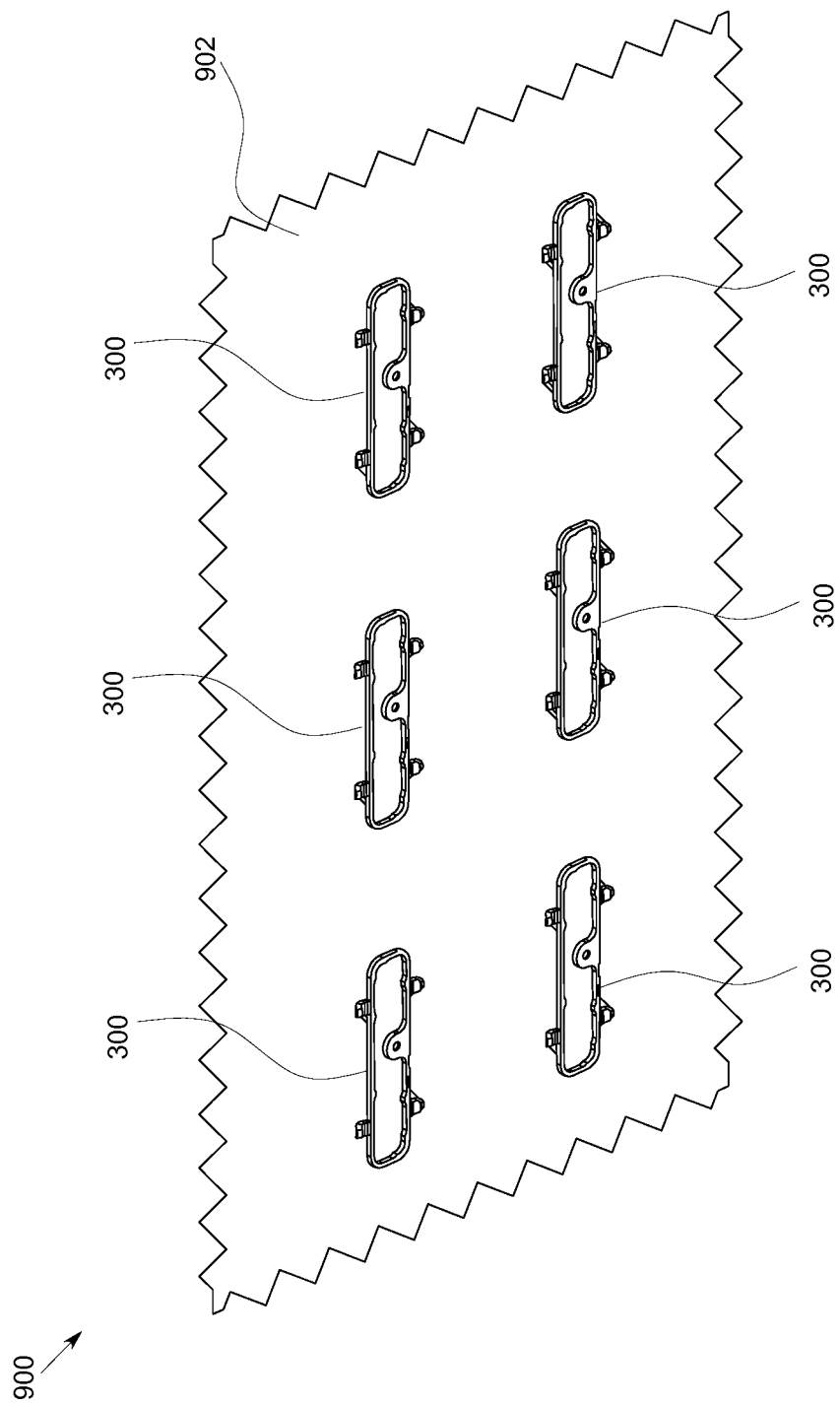
FIG. 9 is a perspective view diagram of multiple inner ferrule portions adhered to a second web, according to an example.
Figure 10:
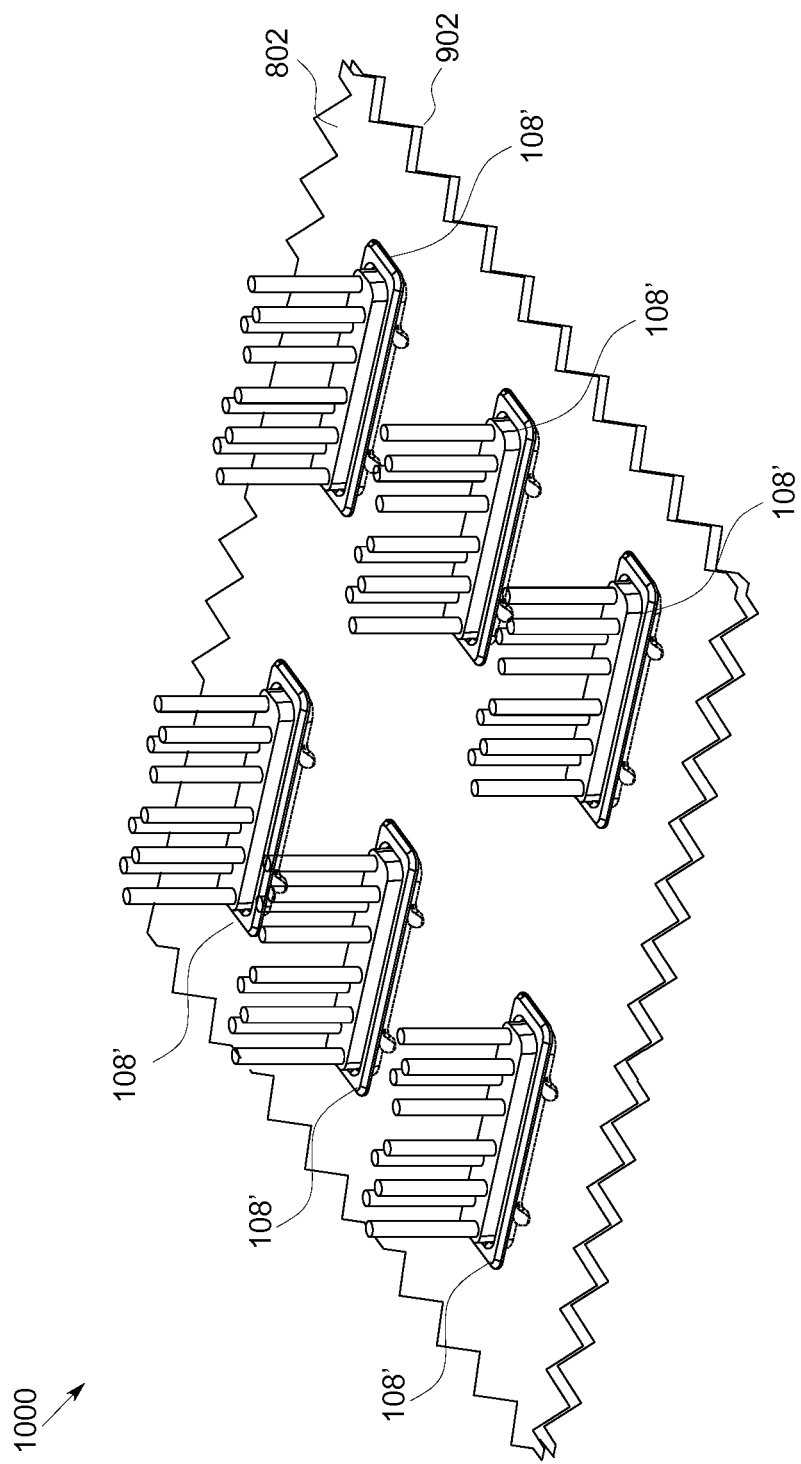
FIG. 10 is a perspective view diagram of multiple ferrules and a first and a second web, according to an example.

The above description has emphasized an example of a procedure with respect to making a single or particular ferrule 108'. However, multiple outer ferrule portions such as the outer ferrule portion 200 (such as shown in FIG. 8) and multiple inner ferrule portions such as the inner ferrule portion 300 (such as shown in FIG. 9) can be serially or concurrently fabricated. This can result in multiple productions of multiple ferrules such as the ferrule 108' (such as shown in FIG. 10).

At 700, stamping an electrically-conductive outer ferrule portion 200 can include stamping a metal sheet. The stamping can be used for forming a plurality of the outer ferrule portion 200, which can be joined by a first web 802 after such stamping. Thus, the first web 802 can carry a plurality of the outer ferrule portion 200.

At 702, stamping an electrically-conductive inner ferrule portion 300 at 702 can include stamping a metal sheet. The stamping can be used for forming a plurality of the inner ferrule portions such as the inner ferrule portion 300, which can be joined by a second web 902 after such stamping. Thus, the second web 902 can carry a plurality of the inner ferrule portion 300.

At 704, the outer ferrule portion 200 can be attached to the respective inner ferrule portion 300. Such attaching can be carried out while the first web 802 is positioned with respect to the second web 902, with the plurality of outer ferrule portion 200 still attached to the first web 802, and with the plurality of inner ferrule portion 300 still attached to the second web 902.

At 706, a plurality of dielectric inserts similar to the dielectric insert 400 can be provided while the first web 802 is positioned with respect to the second web 902. Also, the plurality of outer ferrule portion 200 can still be attached to the first web 802. Further, the plurality of inner ferrule portions such as the inner ferrule portion 300 can still be attached to the second web 902.

Figure 11:
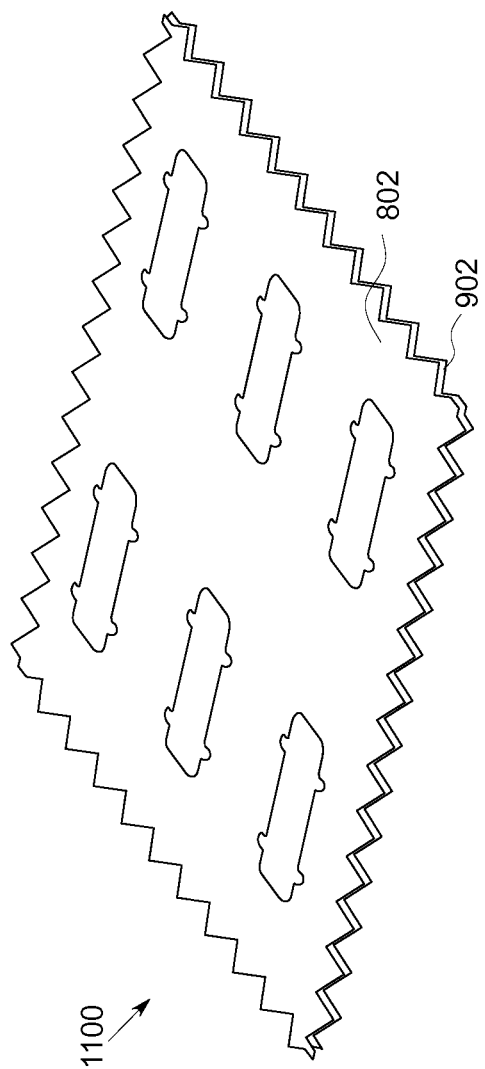
FIG. 11 is a perspective view diagram of a first and a second web with ferrules stamped out, according to an example.
Figure 12:
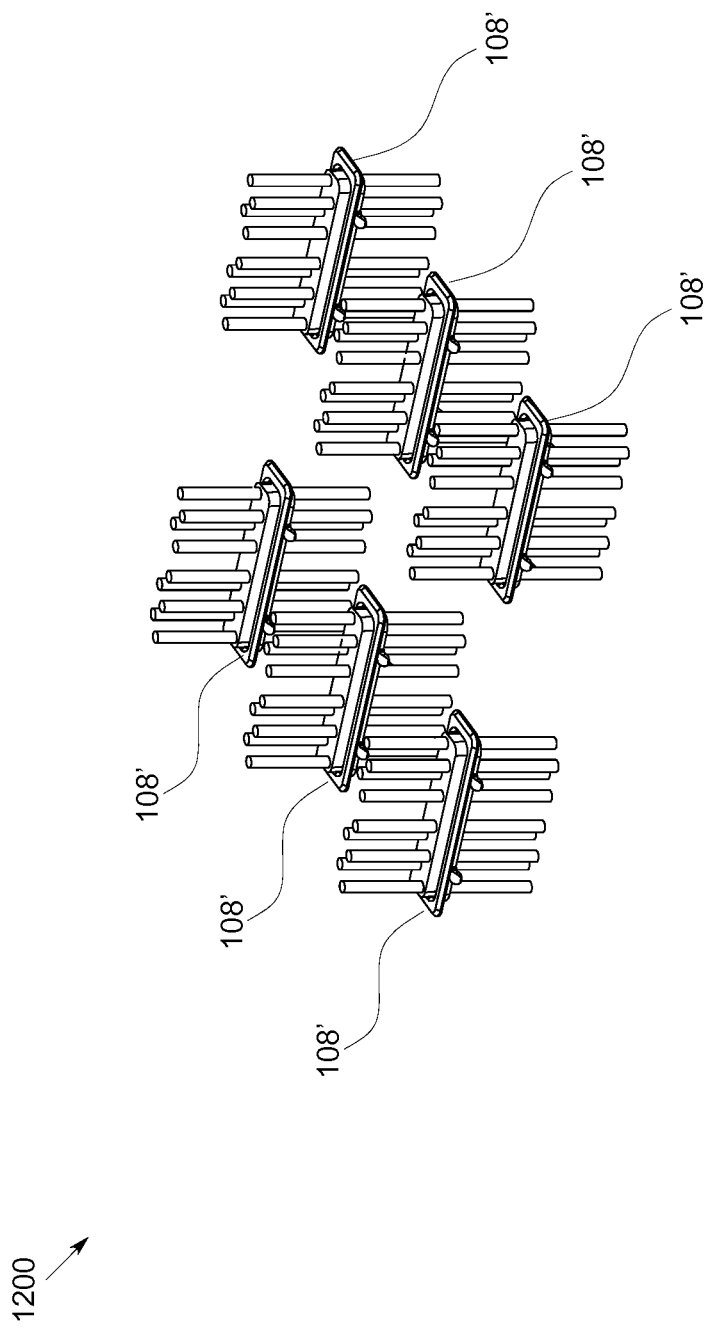
FIG. 12 is a perspective view diagram of multiple ferrules separated from the first and the second web of FIG. 11.

At 708, a plurality of one or more conductors 502 can be provided through respective dielectric insert 400 while the plurality of outer ferrule portion 200 can be still attached to the first web 802 and the plurality of inner ferrule portion 300 can be still attached to the second web 902. The respectively individually attached outer ferrule portion 200 and the inner ferrule portion 300 can be separated from the first web 802 and second web 902, respectively (such as shown in FIGS. 11 and 12). The respectively attached outer ferrule portion 200 and the inner ferrule portion 300 can be disposed within the first passage 116 of a housing 104 of the IMD 100 (such as discussed above). Thus, inner ferrule portion 300 can bias against an interior portion 112 of the housing 104. This can help to draw the outer ferrule portion 200 toward an exterior portion 114 of the housing 104 of the IMD 100, which can help provide a tight seal therebetween. The outer ferrule portion 200 can be further attached and sealed to the exterior portion 114 of the housing 104 of IMD 100.

Figure 13A:
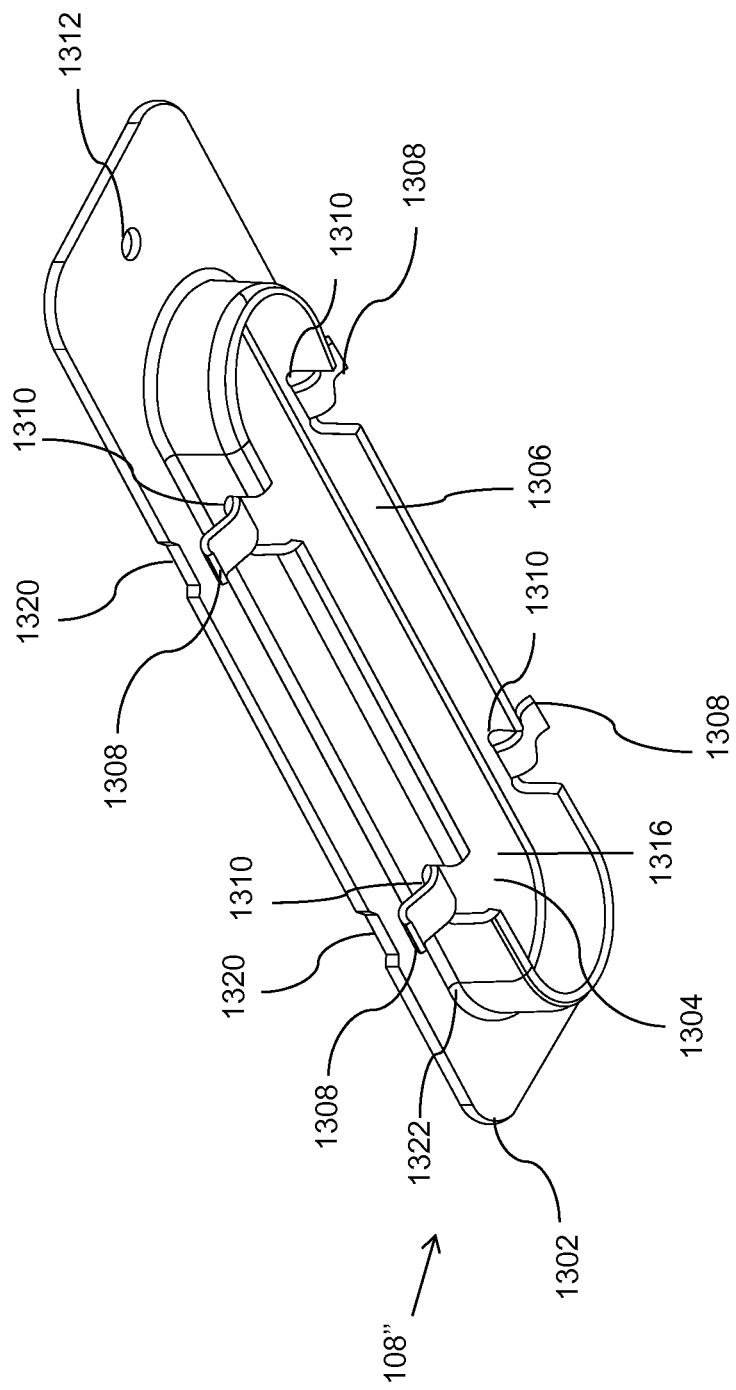
FIG. 13A is a perspective view of a one-piece ferrule, according to an example.

FIG. 13A is a perspective view illustrating generally, by way of an example, but not by way of limitation, a ferrule 108". The ferrule 108" can be a one-piece ferrule referred to as ferrule 108". The ferrule 108" can be used for providing electrical communication through a housing 104 of an IMD 100, which can be metallic and/or hermetically sealed 1304 as discussed herein. The one-piece ferrule 108" can be stamped from a suitable material, such as sheet metal, or can be formed in another way. The one-piece ferrule 108" can include or can be composed of an electrically-conductive biocompatible material such as titanium. One or more other materials such as one or more of niobium, niobium-titanium alloy, titanium-6Al-4V alloy, platinum, iridium, molybdenum, zirconium, tantalum, vanadium, tungsten, palladium, nickel super alloy, and alloys, mixtures, and their alloys can be used to form the one-piece ferrule 108". The one-piece ferrule 108" can be shaped like a rectangular frame or can have another shape. Although not a requirement, the one-piece ferrule 108" can be made of a biocompatible material, such as of the same material as the housing 104 of the IMD 100 such as for facilitating attachment to the housing 104. The ferrule 108" can be affixed or otherwise coupled to the housing 104 and can extend partially within the first passage 116 (e.g., between the interior and exterior portions 112 and 114, respectively, of the housing 104).

The one-piece ferrule 108" can include a drawn or extruded or otherwise formed seat portion 1322. The seat portion 1322 can be sized or shaped or otherwise configured to fit within the first passage 116. A snug fit can be provided, which can help form the hermetic seal 1404 between the seat portion 202 and the first passage 116 of the housing 104. The snug fit can permit welding or brazing the electrically-conductive one-piece ferrule 108" to the exterior portion 114 of the housing 104. The ferrule 108" can include an exterior flange 1302 also referred to as the flange 1302 that can be configured to abut an exterior portion 114 of the metallic housing 104 such that the exterior flange 1302 can define an exit opening 1316.

The flange 1302 can include at least one carrier flash 1320. The carrier flash 1320 can form an integral or monolithic portion of the one-piece ferrule 108". FIG. 13A depicts an example in which the carrier flash 1320 is provided at two distinct opposite locations. However, the carrier flash 1320 can be provided at more than two or less than two locations. The spacing between the carrier flash 1320 placed at distinct locations can vary as desired. The carrier flash 1320 can be a remnant of a progressive die stamping operation.

The one-piece ferrule 108" can further include a tunnel 1304 that can extend from the exterior flange 1302. The tunnel 1304 can be shaped like an oval frame or can have another shape. The tunnel 1304 can define a tunnel interior 1306 that can extend away from the exit opening 1316 and can terminate at an inlet opening 1318 of the one-piece ferrule 108". The tunnel 1304 can be formed by a process comprising drawing a sheet away from the flange 1302. The tunnel 1304 can be sized to conform to the first passage 116 through the housing. The tunnel 1304 can be notched along its length, away from the exit opening 1316, such that at least one interior tab 1308 can extend away from a notch 1310. The at least one interior tab 1308 can extend away from the tunnel interior 1306. The at least one interior tab 1308 can be one of a plurality of interior tabs disposed around the tunnel 1304. The tabs can be formed before or after the tunnel is bent or rolled proximal the inlet opening 1318.

FIG. 13A depicts an example in which the ferrule 108" can include one or more interior tabs 1308, and corresponding notches 1310, 1308, and 1310. The at least one interior tab 1308 can be configured to exert a bias against the metallic housing 104 while the exterior flange 1302 can abut the metallic housing 104. The at least one interior tab 1308 can be bent from material comprising the tunnel 1304. The at least one interior tab 1308 can be made of a flexible or resilient material that can be flexed (e.g., inelastically deformed to assume and retain a new shape) upward or away from the tunnel of the ferrule 108" during the stamping process. The ferrule 108" can include an electrically insulative insert similar to the dielectric insert 400 disposed at least partially inside the tunnel 1304. The hermetic seal 1404 can include gold disposed between the electrically insulative insert 400 and the tunnel 1304.

A system for providing electrical communication can include the IMD 100. The IMD housing 104 can define the interior 112 and the first passage 116 that can extend from the exterior 114 of the IMD housing 104 to the interior 112. The IMD 100 can further include the one-piece ferrule 108" that can be made of a biocompatible material. The ferrule 108" can be conformed to and joined to the first passage 116 such that the ferrule 108" can extend from the exterior 114 to the interior 112 of the IMD housing 104. The ferrule 108" can include the exterior flange 1302 that can be configured to abut the exterior portion 114 of the housing 104 such that the exterior flange 1302 can define the exit opening 1316. The ferrule 108" can further include the tunnel 1304 extending from the exterior flange 1302. The tunnel 1304 can define the tunnel interior 1306, which can extend away from the exit opening 1316 and can terminate at the inlet opening 1318 of the ferrule 108". The ferrule 108" can include at least one interior tab 1308 that can extend away from the tunnel interior 1306. The at least one interior tab 1308 can be configured to exert a bias against the housing 104 while the exterior flange 1302 can abut the housing 104. The ferrule 108" can include the electrically insulative insert 400 disposed at least partially inside the tunnel 1304 and the hermetic seal 1404 disposed between the electrically insulative insert 400 and the tunnel 1304.

Figure 13B:
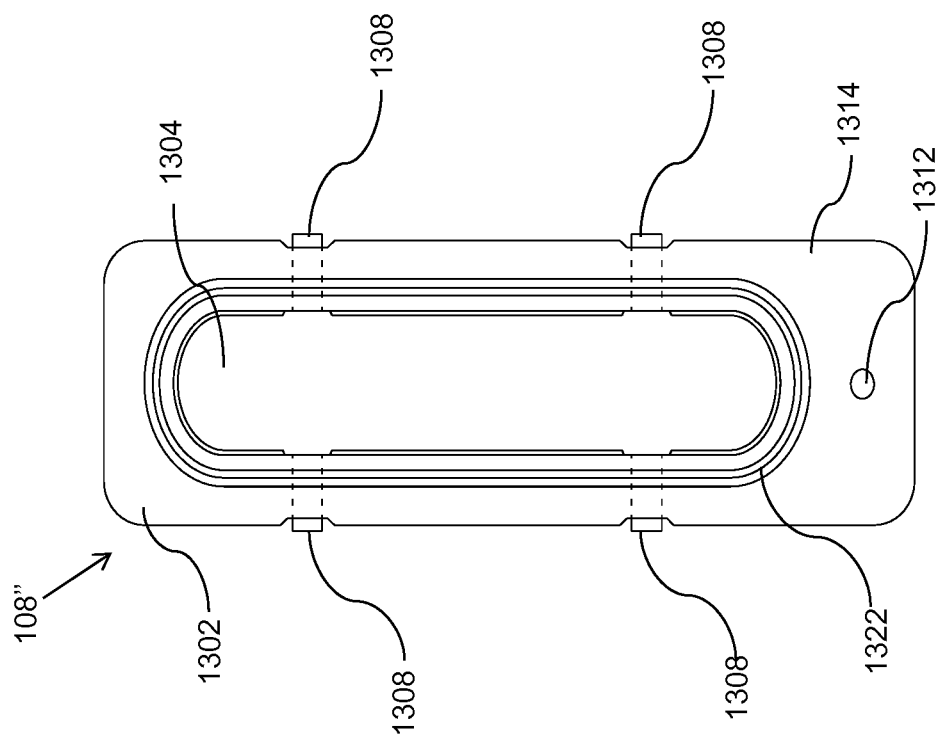
FIG. 13B is a top view diagram of the one-piece ferrule of FIG. 13A.

FIG. 13B is a top view diagram of an example of the one-piece ferrule 108". A top surface 1314 of the exterior flange 1302 can define a recess 1312, such that the recess 1312 encircles the exit opening 1316. The hermetic seal 1404 can further substantially fill the recess 1312 on the top surface 1314 of the exterior flange 1302 as illustrated in FIG. 13B.

Figure 13C:
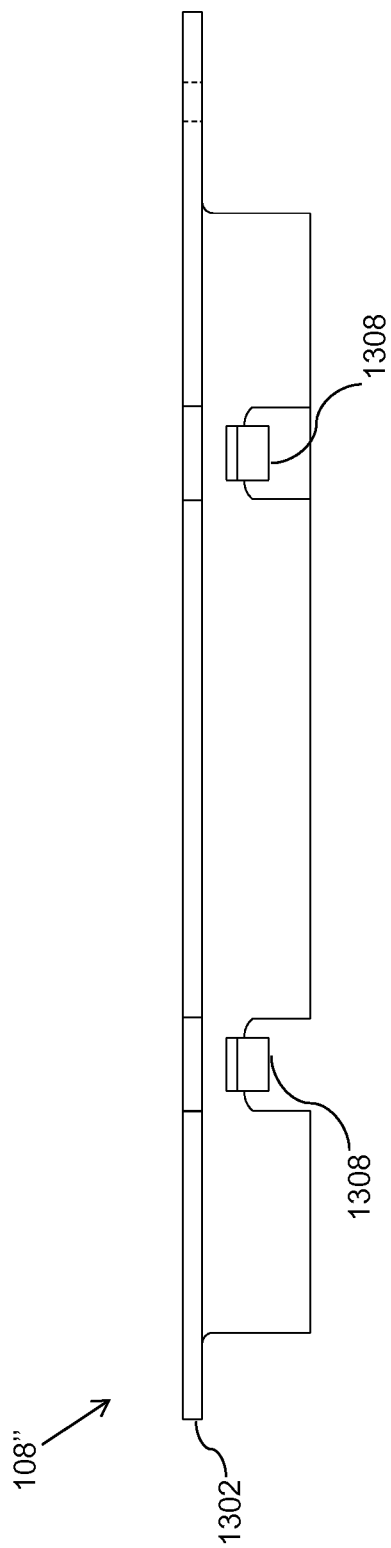
FIG. 13C is a front view diagram of the one-piece ferrule of FIG. 13A.
Figure 13D:
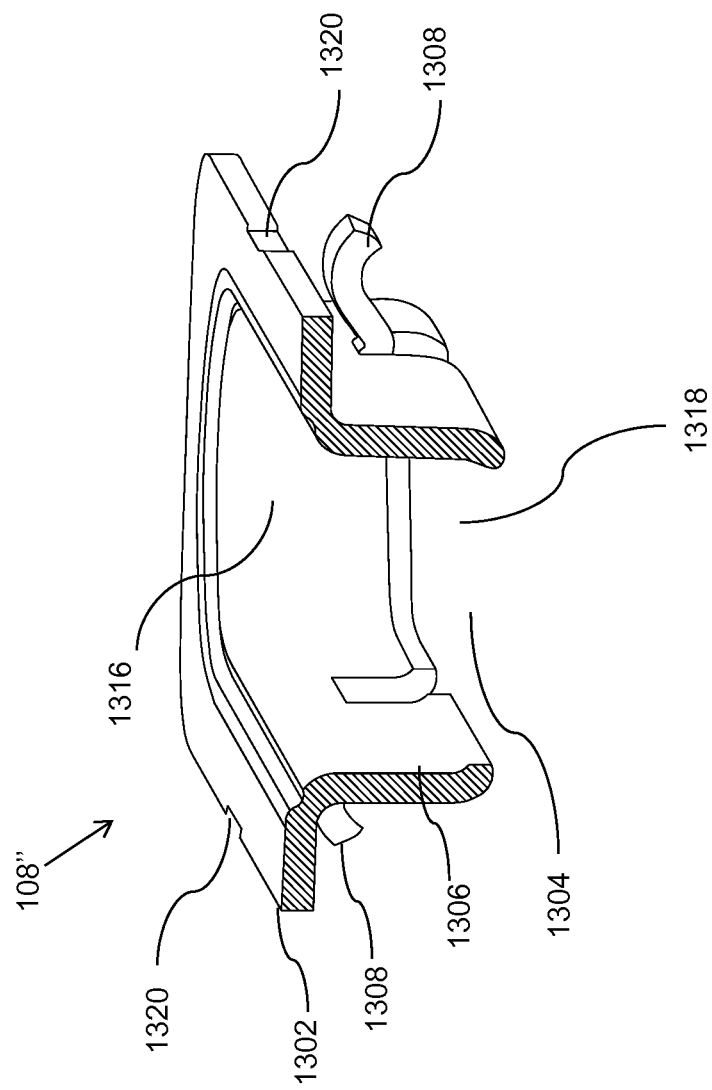
FIG. 13D is a perspective view diagram of a part of the one-piece ferrule of FIG. 13A.

FIG. 13C is a front view of an example of the one-piece ferrule 108". FIG. 13D is a cross sectional perspective view diagram of an example of a part of the one-piece ferrule 108". The ferrule 108" can include or can be composed of the electrically-conductive, biocompatible material such as titanium, similar to the material used to construct the housing 104 of the IMD 100. The ferrule 108" can include the exterior flange 1302 that can be configured to abut the exterior portion 114 of the metallic housing 104 such that the exterior flange 1302 can define the exit opening 1316 (as illustrated in FIG. 9D). The one-piece ferrule 108" can further include the tunnel 1304 that can extend from the exterior flange 1302. The tunnel 1304 can define the tunnel interior 1306 that can extend away from the exit opening 1316 and can terminate at an inlet opening 1318 of the ferrule 108".

Figure 13E:
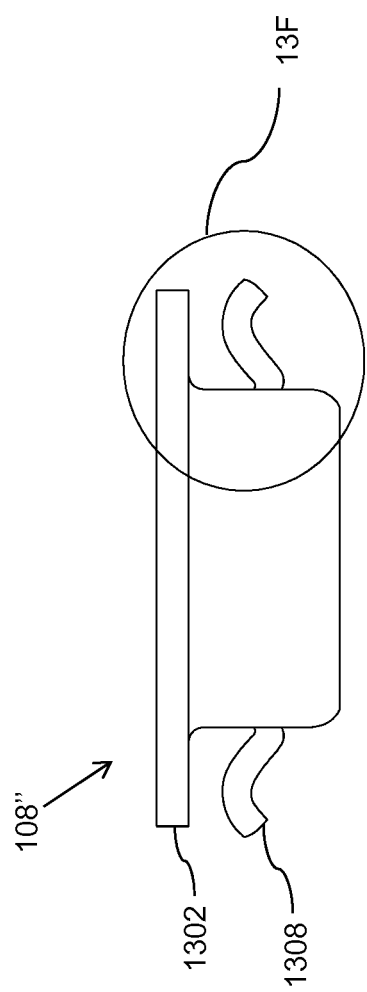
FIG. 13E is a side view diagram of the one-piece ferrule of FIG. 13A.
Figure 13F:
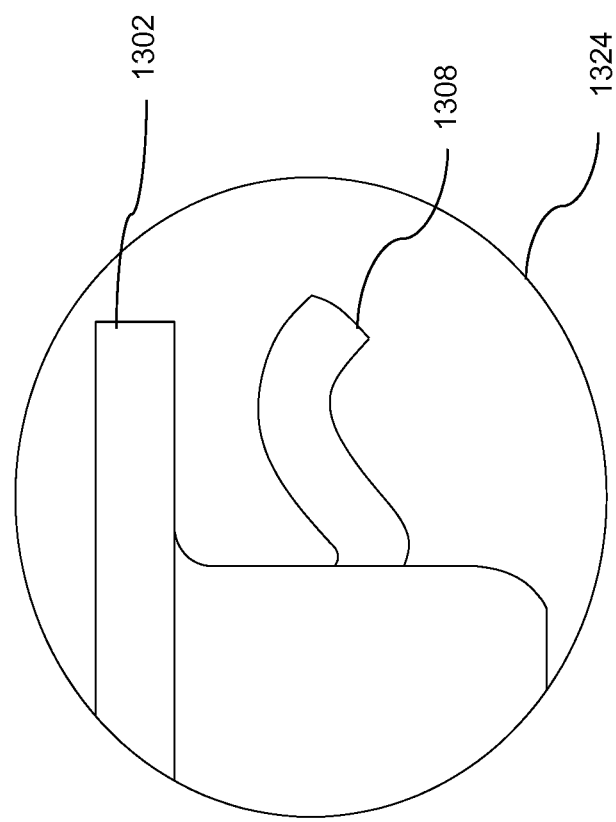
FIG. 13F is an enlarged view of the portion marked 13F in FIG. 13E, according to an example.

FIG. 13E is a side view diagram of an example of the one-piece ferrule 108". FIG. 13F is an enlarged view of an example of a marked portion 13F of the one-piece ferrule 108" of FIG. 13E. The enlarged view of the exterior flange 1302 and the at least one interior tab 1308 is illustrated in FIG. 12F. The at least one interior tab 1308 can include a flex tab that can extend laterally outward from the tunnel 1304 (as shown in FIG. 13F) toward a portion of the interior portion 112 of the housing 104 adjacent the first passage 116. A bias can urge the tab 1308 against the portions of the housing 104 of the IMD 100, such as to draw the one-piece ferrule 108" toward or against the exterior portion 114 of the housing 104. The biasing force can aid in holding the one-piece ferrule 108" flush against the exterior portion 114 of the housing 104 and can help secure the one-piece ferrule 108" such as during welding or other hermetically-sealing or affixation of the one-piece ferrule 108" to the housing 104 of the IMD 100. The tunnel 1304 can be formed by a process such as drawing a sheet away from the flange 1302. The tunnel 1304 can be sized to conform to the first passage 116 through the housing 104.

Figure 14A:
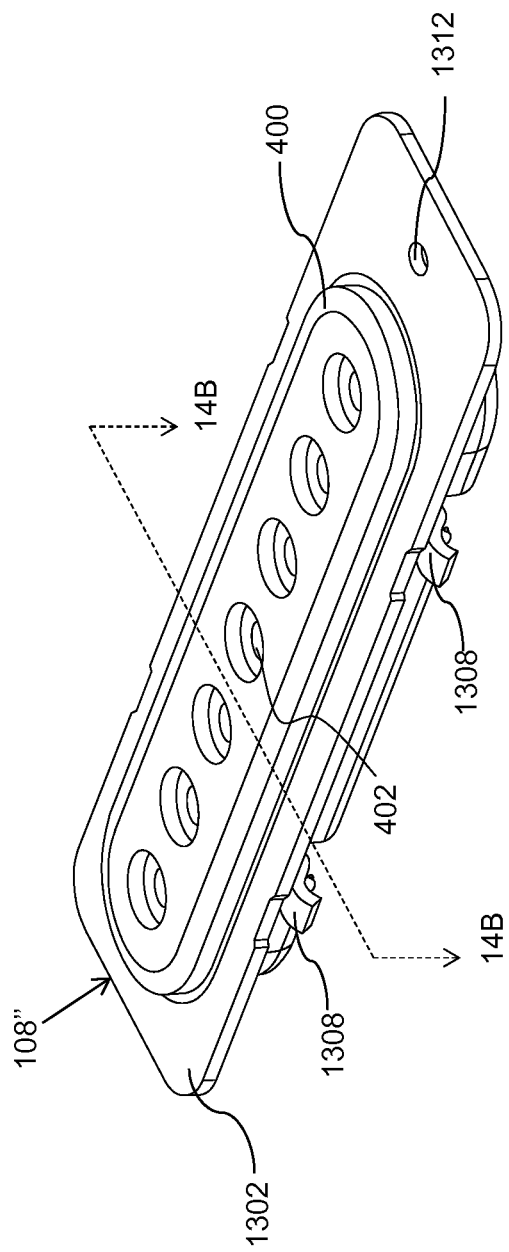
FIG. 14A is a perspective view diagram of an electrical insulative insert placed in a one-piece ferrule, according to an example.

FIG. 14A is a perspective view diagram of an example of the electrically insulative insert 400 placed in the one-piece ferrule 108". An example of the one-piece ferrule 108" has been described above in detail in conjunction with FIG. 13A. FIG. 14A depicts an example that can include one or a plurality of lumens such as through lumens 402. The lumens 402 can pass the respective electrical conductors. More or a fewer through lumens 402 or conductors, than that shown in FIG. 14A, can be used. The ferrule 108" can further include the electrically insulative insert 400 disposed at least partially inside the tunnel 1304 and the hermetic seal 1404 disposed between the electrically insulative insert 400 and the tunnel 1304, such as shown in FIG. 14A.

The dielectric insert 400 can be metallized. Metalizing can be accomplished by sputtering a thin layer of metal such as titanium onto the dielectric insert 400. One or more other metals can also be used in metalizing. The electrically insulative insert 400 can be brazed to the ferrule 108". Metalizing the dielectric insert 400 can improve a brazing operation to join the dielectric insert 400 to another component, such as the ferrule 108". The dielectric insert 400 can operate to electrically isolate the electrical connection of the at least one of the conductors 502 passing through the lumens 402 from the electrically-conductive ferrule 108".

The conductive portions isolated by the non-conducting dielectric insert 400 can provide a capacitor structure. The capacitive structure can be disposed within the housing 104 and partially disposed within the ferrule 108". The capacitive structure can be operatively coupled to a distal portion of the conductor. This capacitor can help filter unwanted electromagnetic interference (e.g., EMI) from passing through the feedthrough to which the ferrule 108" can be coupled. The dielectric insert 400 can include or can be composed of a ceramic material such as one or more of alumina, co-fired alumina, boron nitride, or another ceramic material. The ceramic material can fit inside the ferrule and can create a hermetic seal 1404.

Figure 14B:
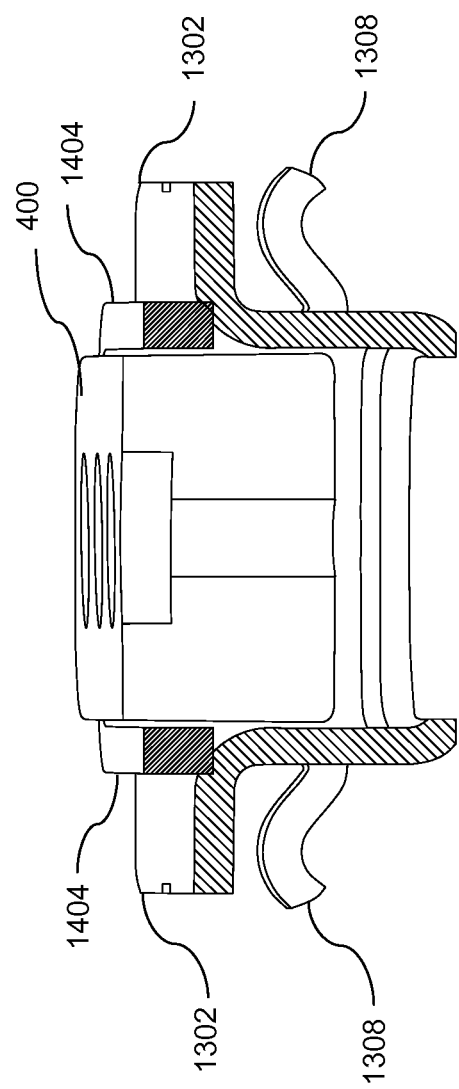
FIG. 14B is a cross sectional side view taken along an axis 14B-14B in FIG. 14A, according to an example.

FIG. 14B is an example of a cross sectional side view diagram taken along an axis 14-14. FIG. 14B shows a part of the electrically insulative insert 400 placed in the one-piece ferrule 108" with the hermetic seal 1404. The hermetic seal 1404 can substantially fill the recess 1312. The electrically insulative insert 400 can be brazed to the ferrule 108". A brazing material can form the hermetic seal 1404 between the electrically insulative insert 400 and the ferrule 108". The brazing material that can be used to maintain the electrically insulative insert 400 within the ferrule 108" can be composed of any suitable braze material or materials. Examples of suitable braze materials include, but are not limited to gold, a gold alloy, or the like. The brazing material can fill in one or more gaps between the above discussed ceramic material and another component. The brazing material can fit inside the ferrule and can create a hermetic seal 1404. The ceramic material can be metallized with titanium. The ceramic material can be metallized on its surface as well as internally, such as through pores. The titanium can bind to the outside layer of the ceramic material, such as alumina, such that it can create a metallized layer that can allow the gold to enter into that layer.

Figure 15A:
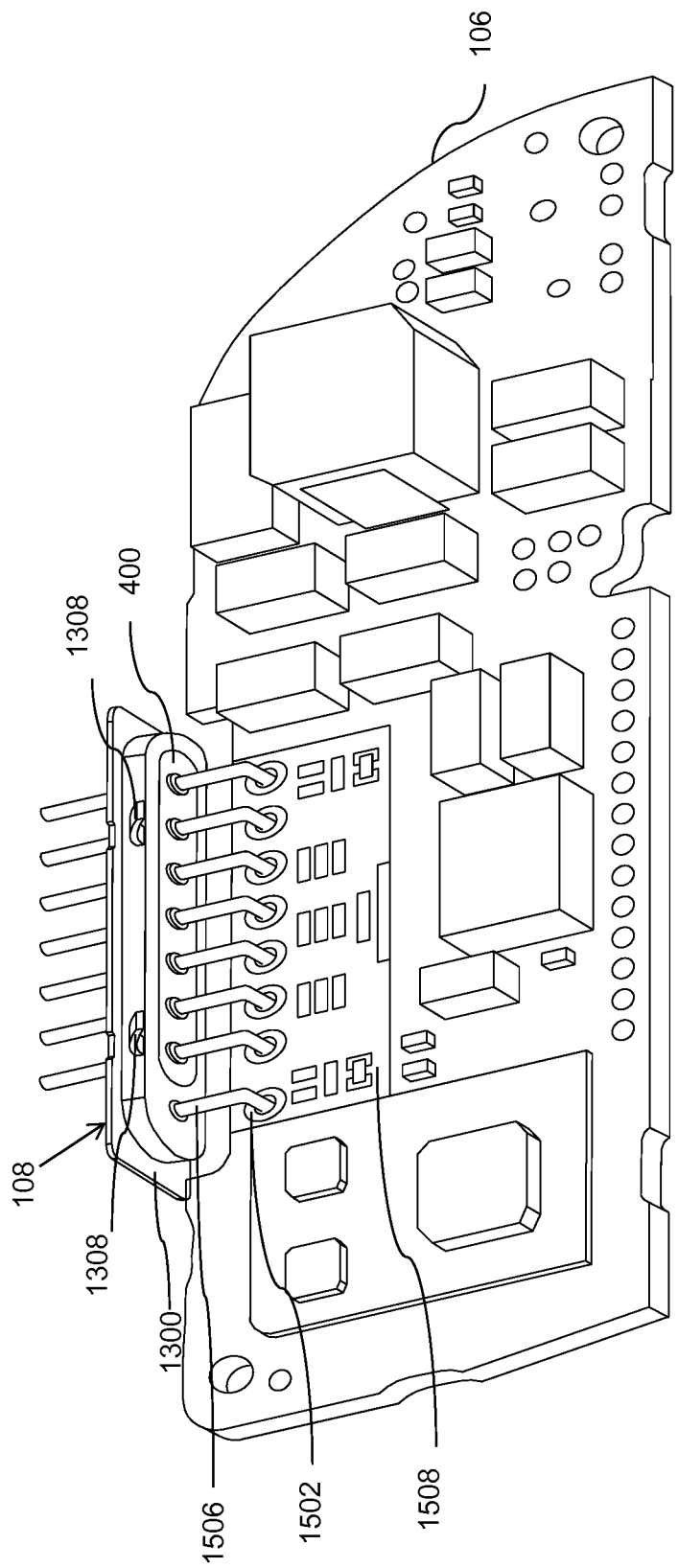
FIG. 15A is a perspective view diagram of a ferrule coupled to a circuit, according to an example.

FIG. 15A is a perspective view diagram of an example of the one-piece ferrule 108" coupled to the circuit 106. The ferrule can be situated on the surface of the circuit 106. The ferrule 108" can be attached to the circuit 106 using a surface mount circuit assembly or populating technique. As illustrated in FIG. 15A, at least one of the conductors 502 can extend through the electrically insulative insert 400 to be coupled to a respective terminal 1502 of a capacitor 1504 disposed on the circuit 106. The capacitor 1504 can be mounted on a capacitor board 1508. The capacitor board 1508 can be mounted flush with the circuit 106, such as to reduce or minimize height is taken up by the capacitor board 1508. The ferrule 108" can include a ground 1506 on the circuit 106.

Figure 15B:
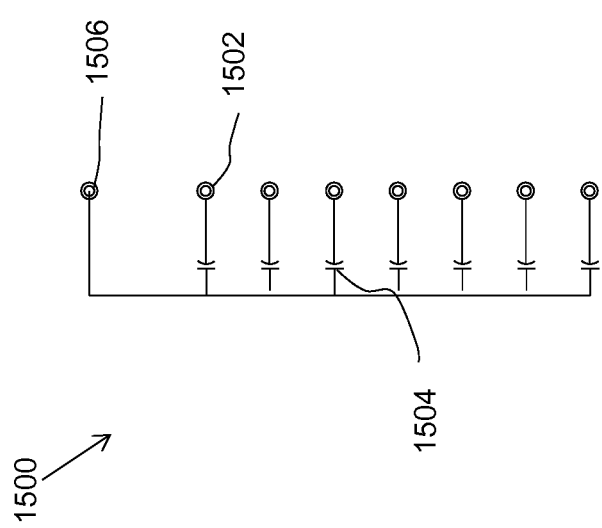
FIG. 15B is a schematic diagram of a ferrule coupled to a circuit, according to an example.

FIG. 15B is a schematic illustrating generally, by way of an example, but not by way of limitation, the one-piece ferrule 108" coupled to the circuit 106. The one-piece ferrule 108" can include an electrically insulative insert 400 that can be disposed at least partially inside the tunnel 1304. At least one of the conductors 502 can extend through the electrically insulative insert 400. The circuit 106 can be coupled to the at least one of the conductors 502. The at least one of the conductors 502 can be one of a plurality of conductors, such as conductors 502. Individual ones of the conductors 502 can be coupled to a respective terminal 1502 of the capacitor 1504 disposed on the circuit 106, such as shown in FIG. 14B. Some of the conductors 502 can be electrically coupled to a common polarity. The at least one of the plurality of conductors 502 can be in electrical communication with the metallic housing 104 and an opposite polarity terminal of each of the respective capacitors 1504. The at least one of the conductors 502 can be one of a plurality of conductors 502 such that the circuit 106 can include a capacitive filter electrical signal carried on the plurality of conductors 502. The at least one of the conductors 502 can be soldered or welded or otherwise electrically and mechanically connected to a conductive pad or the respective terminal 1502 on the circuit 106.

FIG. 15B shows an example of circuitry for providing the functionality of the IMD 100. The IMD 100 can include a pacemaker, a ICD, a defibrillator, or another medical device. FIG. 15B can include protection circuitry for protecting the IMD 100 from external electrical interference such as voltage or current surges at inputs provided by the feedthrough into the interior portion 112 of the housing 104. The protection circuitry can include a capacitive filter. The capacitive filter can include a power supply filter that can be used to filter signals from other circuitry such as high voltage signals.

Figure 16:
FIG. 16 is a diagram of a method of manufacturing a one piece ferrule assembly including a one piece ferrule, according to an example.

FIG. 16 is a diagram of an example of a method of manufacturing the one-piece ferrule 108" assembly. At 1600, the ferrule 108" can be formed by a stamping process, such as progressive-die stamping. The one-piece ferrule 108" can be electrically conductive and can be formed to include one or more stamped sheet metal portions. This can include stamping the titanium or other metal sheet, such as to form the one or more stamped sheet metal portions of the ferrule 108" for creating the first passage 116 through the sheet, which can be stamped to be sized or shaped or otherwise configured to be located toward and welded or brazed to the interior 112 and exterior 114 walls of the housing 104. At 1600, the sheet can be stamped to define the flange 1302, such as with the tunnel 1304 extending away from the flange 1302. The flange 1302 can be configured to abut the exterior portion 114 of the housing 104 (such as discussed in conjunction with FIG. 13).

At 1602, the tunnel 1304 can be cut or extruded that can define the at least one tab 1308, thereby creating at least one tab 1308 on the sides. The tunnel 1304 can be shaped like an oval frame, or can have another shape. The tunnel 1304 can be notched along its length, away from the opening such that at least one interior tab 1308 can extend away from a notch 1310. The ferrule 108" can include four interior tabs 1308, e.g., similar to the at least one interior tab 1308 and four notches, e.g., similar to the notch 1310, but more or fewer tabs 1308 or notches 1310 can be employed.

At 1604, the interior tab 1308 can be bent away from the tunnel 1304, such as toward a perimeter of the flange 1302. The at least one interior tab 1308 can extend away from the tunnel interior 1306.

At 1606, the inlet opening 1318 from the tunnel 1304 can be excised. The inlet opening 1318 can be in communication with an opening such as the exit opening 1316 around which the flange 1302 extends. The flange 1302 defines the exit opening 1316.

At 1608, the electrically insulative insert 400 can be inserted in the tunnel 1304. The dielectric insert 400 can be provided such that the dielectric insert 400 is captured partially within the frame provided by the ferrule 108" (such as discussed above in FIG. 12).

At 1610, at least one of the conductors 502 can be disposed through the electrically insulative insert 400. The at least one of the conductors 502 can pass through a respective aperture or lumens 402 in the dielectric insert 400.

At 1612, the electrically insulative insert 400 can be sealed to the at least one of the conductors 502. The conductors 502 that are located within the respective aperture or lumen 210 through the dielectric insert 400 can be hermetically sealed within the aperture or lumen 210 in the dielectric insert 400, such as by brazing or another technique suitable for such sealing. The braze material used to maintain the electrically insulative insert 400 within the ferrule 108" can be composed of any suitable material or materials. Examples of suitable braze materials include, but are not limited to, gold, a gold alloy, or the like.

At 1614, the electrically insulative insert 400 can be sealed to the ferrule 108". The dielectric insert 400 can be metallized. Metalizing can be accomplished by sputtering the thin layer of metal such as titanium onto the dielectric insert 400. One or other metals can be used in metalizing. Metalizing the dielectric insert 400 can improve a brazing operation to join the dielectric insert 400 to another component, such as the ferrule 108" (such as discussed in conjunction with FIG. 14A).

The method can further include pinching the wall of the housing 104 between the at least one tab 1308 and the flange 1302, such as under a bias exerted by elastic deformation of the tab 1308. The at least one interior tab 1308 can be made of a flexible or resilient material that can be flexed. The method can include forming the housing 104 by joining two cup-shaped housing shells 118A and 118B. The method can include joining the two cup-shaped housing shells 118A and 118B such that the two cup-shaped housing shells 118A and 118B can define the first passage 116 that can extend from the exterior 114 of the housing 104 to the interior 112 of the housing 104. The method can include disposing two cup-shaped housing shells 118A and 118B together to define the passage. One of the shells can include a stepped portion sized to fit in the other shell. At least one tab 1308 can bias the ferrule 108", such as to adjust the flange 1302 against the exterior 114 of the two cup-shaped housing shells 118A and 118B. The method can include joining the flange 1302 to the housing 104 by a welding technique such as laser welding.

A potential advantage of the ferrule 108' can be that it can be provided in two separate portions, (e.g., the outer portion 200 and inner ferrule portion 300), each of which can be manufactured by stamping. The stamped outer and inner ferrule portions 200 or 300 can remain on a web, such as to help improve throughput or otherwise aid in the later steps of the manufacturing process. Such a process can provide increased production throughput by using a web, and optionally, a reel-to-reel process to input one or more webs and output finished ferrules.

Another potential advantage of the stamped outer and inner ferrule portions 200 or 300 can be that the stamped outer or inner ferrule portions 200 or 300 can provide lower component cost than a more time-consuming precision machining process. This can lower the expense to manufacture a device using the ferrule.

Another potential advantage of the stamped outer and inner ferrule approach can be that the stamped outer and inner ferrule portions can potentially assist in a better welding of the stamped outer and inner ferrule portions to the implantable medical device housing.

A potential advantage of the ferrule described herein can be that it can be provided as one-piece, such as can be manufactured by stamping. This one-piece ferrule can be made in a progressive stamping process, which can yield high throughput with low cost.

A potential advantage of the one-piece ferrule can be that it can fulfill a basic function of some ferrule designs, e.g., can provide a hermetic seal for the device with an electrical conductor passing therethrough. The one-piece ferrule can use one integral or monolithic stamped piece.

A potential advantage of the one-piece ferrule can be that it can hold case halves and ferrule flange 1302 together, such as to provide contact for welding or to provide a cavity, such as for ceramic or gold braze.

VARIOUS NOTES & EXAMPLES

Example 1 can include or use an apparatus for providing electrical communication through housing that is metallic and hermetically sealed. The subject matter can include a one-piece ferrule that is biocompatible. The ferrule can be configured to be located at least partially within a passage extending from an interior and exterior of an implantable medical device housing to an exterior. The ferrule can include an exterior flange configured to abut an exterior surface of the metallic housing, the exterior flange defining an exit opening. The ferrule can include a tunnel extending from the exterior flange, the tunnel defining a tunnel interior extending away from the exit opening and terminating at inlet opening of the ferrule. The ferrule can include at least one interior tab extending away from an interior of the tunnel, the at least one interior tab configured to exert a bias against the metallic housing while the exterior flange abuts the metallic housing. The ferrule can include an electrically insulative insert disposed at least partially inside the tunnel. The ferrule can include a hermetic seal disposed between the electrically insulative insert and the tunnel.

Example 2 optionally includes the subject matter of any of the preceding examples, wherein the flange can include at least one carrier flash.

Example 3 optionally includes the subject matter of any of the preceding examples, wherein the tunnel can be notched along its length, away from the opening, with the at least one interior tab extending away from the notch.

Example 4 optionally includes the subject matter of any of the preceding examples, wherein the at least one interior tab is bent from material comprising the tunnel.

Example 5 optionally includes the subject matter of any of the preceding examples, wherein the at least one interior tab is one of a plurality of interior tabs disposed around the tunnel.

Example 6 optionally includes the subject matter of any of the preceding examples, wherein the hermetic seal includes gold.

Example 7 optionally includes the subject matter of any of the preceding examples, wherein a top surface of the exterior flange defines a recess encircling the exit opening.

Example 8 optionally includes the subject matter of any of the preceding examples, wherein the hermetic seal substantially fills the recess.

Example 9 optionally includes the subject matter of any of the preceding examples, wherein the at least one conductor is one of a plurality of conductors, and wherein each of the conductors is coupled to a respective terminal of a capacitor disposed on the circuit.

Example 12 optionally includes the subject matter of any of the preceding examples, wherein some of the conductors are electrically coupled to a common polarity.

Example 13 optionally includes the subject matter of any of the preceding examples, wherein at least one of the plurality of conductors is in electrical communication with the metallic housing and an opposite polarity terminal of each of the respective capacitors.

Example 14 optionally includes the subject matter of any of the preceding examples, wherein the at least one conductor is one of a plurality of conductors, wherein the circuit comprises a capacitive filter electrical signals carried on the plurality of conductors.

Example 15 optionally includes the subject matter of any of the preceding examples, wherein the ferrule is stamped.

Example 16 optionally includes the subject matter of any of the preceding examples, wherein the at least one interior tab is a flex tab extending laterally outward from the tunnel and toward and against a portion of an interior wall of the housing adjacent the passage.

Example 17 optionally includes the subject matter of any of the preceding examples, wherein the tunnel is formed by a process comprising drawing a sheet away from the flange.

Example 18 optionally includes the subject matter of any of the preceding examples, wherein the tunnel is sized to conform to the passage through the housing.

Example 19 optionally includes the subject matter of any of the preceding examples, including forming a ferrule, by stamping a sheet to define a flange, with a tunnel extending away from the flange. The example can include cutting the tunnel to define at least one tab. The example can include bending the tab away from the tunnel, toward a perimeter of the flange. The example can include excising an inner opening from the tunnel, the inner opening in communication with an opening around which the flange extends. The example can include inserting an electrically insulative insert in the tunnel. The example can include disposing a conductor through the electrically insulative insert. The example can include sealing the electrically insulative insert to the conductor. The example can include sealing the electrically insulative insert to the ferrule.

Example 20 optionally includes the subject matter of any of the preceding examples, wherein stamping includes progressive-die stamping.

Example 21 optionally includes the subject matter of any of the preceding examples, including pinching a wall of a housing between the at least one tab and the flange under a bias exerted by elastic deformation of the tab.

Example 22 optionally includes the subject matter of any of the preceding examples, including forming the housing by joining two cup-shaped housing shells.

Example 23 optionally includes the subject matter of any of the preceding examples, wherein pinching the passage is irregular, with opposing steps defined between the two cup-shaped housing shells, wherein the at least one tab biases the ferrule to adjust the flange against the exterior of the two cup-shaped housing shells.

Example 25 optionally includes the subject matter of any of the preceding examples, wherein metalizing includes sputtering metal onto the electrically insulative insert.

Example 30 optionally includes the subject matter of any of the preceding examples, wherein the metal includes titanium.

Example 31 optionally includes the subject matter of any of the preceding examples, wherein sealing includes brazing.

Example 32 optionally includes the subject matter of any of the preceding examples, wherein brazing includes brazing with gold.

Example 33 optionally includes a system including an implantable medical device housing defining an interior and a passage extending from an exterior of the implantable medical device housing to the interior. The example can include a one-piece ferrule that is biocompatible, the ferrule conformed to and joined to the passage, the ferrule extending from the exterior to the interior of the implantable medical device housing. The ferrule can include an exterior flange configured to abut an exterior surface of the housing, the exterior flange defining an exit opening. The example can include a tunnel extending from the exterior flange, the tunnel defining a tunnel interior extending away from the exit opening and terminating at inlet opening of the ferrule. The example can include at least one interior tab extending away from an interior of the tunnel, the at least one interior tab configured to exert a bias against the housing while the exterior flange abuts the housing. The example can include an electrically insulative insert disposed at least partially inside the tunnel. The example can include a hermetic seal disposed between the electrically insulative insert and the tunnel.

Example 34 optionally includes the subject matter of any of the preceding examples, including a weld attaching the outer ferrule portion to the exterior portion of the housing.

Example 35 can include a medical device including a housing, including an interior portion, an exterior portion, and a first passage between the interior and exterior portions of the housing, the housing configured to carry and hermetically enclose an electronic circuit. The example can include a capacitive filter ferrule, configured to be located at least partially within the first passage between the interior and exterior portions of the housing to allow capacitively-filtered passage of an electrical connection there between, the capacitive filter ferrule including. The example can include an electrically-conductive outer ferrule portion, configured to be located toward the exterior portion of the housing. The example can include an inner ferrule portion, configured to be located toward the interior portion of the housing, the inner ferrule portion non-integrally formed with the outer ferrule portion but attached to the outer ferrule portion. The example can include the electrical connection. The example can include a dielectric plug, electrically isolating the electrical connection from the electrically-conductive outer ferrule portion.

Example 36 can optionally include the subject matter of example 35, wherein the inner ferrule portion includes a flexing flange extending laterally outward within the interior portion of the housing and also extending toward and biasing against a portion of an interior wall of the housing adjacent to the first passage between the interior and exterior portions of the housing.

Example 37 can optionally include the subject matter of any of examples 35-36, wherein the outer ferrule portion includes a stamped sheet metal portion that is sized and shaped to accept a portion of the dielectric plug there within and to fit snugly at least partially within the first passage between the interior and exterior portions of the housing. In the example, the inner ferrule portion can include a stamped sheet metal portion that is sized and shaped to accept a portion of the dielectric plug there within and to provide the flexing flange.

Example 38 can optionally include the subject matter of any of examples 35-37, wherein the outer ferrule portion is welded to the inner ferrule portion.

Example 39 can optionally include the subject matter of any of examples 35-38, wherein the outer ferrule portion is vacuum-fused to the inner ferrule portion.

Example 40 can optionally include the subject matter of any of examples 35-39, wherein the outer ferrule portion includes a drawn or extruded seat portion that is sized and shaped to fit within the first passage.

Example 41 can optionally include the subject matter of any of examples 35-40, wherein the inner ferrule portion is electrically-conductive and includes an electrically-conductive tab extending laterally toward an interior of the first passage between the interior and exterior portions of the housing, the electrically-conductive tab including a second passage capable of passing an electrical conductor there though so as to permit an electrical connection between the electrical conductor and the electrically-conductive tab.

Example 42 can optionally include the subject matter of any of examples 35-41, wherein the dielectric plug includes a plurality of through lumens carrying respective electrical conductors.

Example 43 can optionally include the subject matter of any of examples 35-42, comprising a weld attaching the outer ferrule portion to the exterior portion of the housing.

Example 44 includes forming an electrically-conductive outer ferrule portion that is sized and shaped to fit about a first passage between the interior and exterior portions of a housing of an implantable medical device such that the outer ferrule portion is located toward the exterior portion of the housing. The example can include forming an inner ferrule portion that is sized and shaped to fit about the first passage between the interior and exterior portions of the housing of the implantable medical device such that the inner ferrule portion is located toward the interior portion of the housing. The example can include attaching the outer ferrule portion to the inner ferrule portion. The example can include providing a dielectric plug at least partially within the outer and inner ferrule portions. The example can include providing an electrical conductor through the dielectric plug.

Example 45 optionally includes the subject matter of any examples 35-44, wherein the forming the inner ferrule portion comprises stamping a sheet to form a flexing flange sized and shaped for extending laterally outward within the interior portion of the housing and also sized and shaped for extending toward and biasing against a portion of an interior wall of the housing adjacent to the first passage between the interior and exterior portions of the housing.

Example 46 optionally includes the subject matter of examples 35-45, wherein forming an electrically-conductive outer ferrule portion comprises stamping a sheet for creating a passage through the sheet, the passage sized and shaped to accept the dielectric plug, and comprising extruding or drawing the sheet to form a seat portion that is sized and shaped to fit within the first passage.

Example 47 optionally includes the subject matter of examples 35-46, wherein providing the dielectric plug comprises providing a plurality of dielectric plugs while the first web is positioned with respect to the second web and while the plurality of outer ferrule portions are still attached to the first web and the plurality of inner ferrule portions are still attached to the second web.

Example 48 optionally includes the subject matter of examples 35-47, wherein the providing the electrical conductor through the dielectric plug comprises providing a plurality of electric conductors through respective dielectric plugs while the plurality of outer ferrule portions are still attached to the first web and the plurality of inner ferrule portions are still attached to the second web.

Example 49 optionally includes the subject matter of examples 35-49, wherein attaching and sealing the outer ferrule portion to the exterior wall of the housing of the implantable medical device comprises welding or brazing the outer ferrule portion to the exterior wall of the housing of the implantable medical device.

Example 50 can optionally include the subject matter of any of examples 35-49, wherein attaching the outer ferrule portions to the respective inner ferrule portions comprises welding the outer ferrule portions to the respective inner ferrule portions.

Example 51 can optionally include the subject matter of any of examples 35-50, wherein attaching the outer ferrule portions to the respective inner ferrule portions comprises vacuum fusing the outer ferrule portions to the respective inner ferrule portions.

Example 52 can optionally include the subject matter of any of examples 35-51, including a housing including an interior portion, an exterior portion, and a first passage between the interior and exterior portions of the housing, the housing configured to carry and hermetically enclose an electronic circuit. The example can include a capacitive filter ferrule, configured to be located at least partially within the first passage between the interior and exterior portions of the housing to allow capacitively-filtered passage of an electrical connection there between, the capacitive filter ferrule including. The example can include an electrical connection. The example can include a dielectric plug. The example can include an electrically-conductive outer ferrule portion, configured to be located toward and welded or brazed to the exterior portion of the housing, wherein the outer ferrule portion includes a stamped sheet metal portion that is sized and shaped to accept a portion of the dielectric plug there within and to fit snugly at least partially within the first passage between the interior and exterior portions of the housing, wherein the dielectric plug, electrically isolates the electrical connection from the electrically-conductive outer ferrule portion. The example can include an inner ferrule portion, configured to be located toward the interior portion of the housing, the inner ferrule portion non-integral with the outer ferrule portion but attached to the outer ferrule portion by welding or vacuum fusing, wherein the inner ferrule portion includes a flexing flange extending laterally outward within the interior portion of the housing and also extending toward and biasing against a portion of an interior wall of the housing adjacent to the first passage between the interior and exterior portions of the housing, wherein the inner ferrule portion includes a stamped sheet metal portion that is sized and shaped to accept a portion of the dielectric plug there within and to provide the flexing flange, wherein the inner ferrule portion is electrically-conductive and includes an electrically-conductive tab extending laterally toward an interior of the first passage between the interior and exterior portions of the housing, the electrically-conductive tab including a second passage capable of passing an electrical conductor there though so as to permit an electrical connection between the electrical conductor and the electrically-conductive tab. The example can include a configuration wherein the dielectric plug includes a plurality of through lumens carrying respective electrical conductors.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. An apparatus for providing electrical communication through a housing that is metallic and hermetically sealed, the apparatus comprising:
   a one-piece ferrule that is biocompatible, the ferrule configured to be located at least partially within a passage into an implantable medical device housing, the ferrule including:
   an exterior flange configured to abut an exterior surface of the metallic housing, the exterior flange defining an exit opening;
   a tunnel extending from the exterior flange, the tunnel defining a tunnel interior extending away from the exit opening and terminating at inlet opening of the ferrule;
   at least one interior tab extending away from an interior of the tunnel in a direction generally aligned with the exterior flange such that a first surface of the at least one interior tab faces the exterior flange and a second, opposite surface of the at least one interior tab faces away from the exterior flange, the at least one interior tab configured to exert a spring bias with the first surface directly against an interior surface of the metallic housing and toward the exterior flange while the exterior flange abuts the exterior surface of the metallic housing to draw the exterior flange toward the exterior surface of the metallic housing;
an electrically insulative insert disposed at least partially inside the tunnel; and
a hermetic seal disposed between the electrically insulative insert and the tunnel.

2. The apparatus of claim 1, wherein the ferrule is a one-piece progressively die stamped monolith including at least one carrier flash.

3. The apparatus of claim 1, comprising at least one conductor extending through the electrically insulative insert.

4. The apparatus of claim 3, comprising a circuit coupled to the at least one conductor.

5. The apparatus of claim 1, wherein the at least one interior tab is a flex tab extending laterally outward from the tunnel and toward and against a portion of an interior wall of the housing adjacent the passage.

6. A system, comprising:
an implantable medical device housing defining an interior and a passage extending from an exterior of the implantable medical device housing to the interior;
a one-piece ferrule that is biocompatible, the ferrule conformed to and joined to the passage, the ferrule extending from the exterior to the interior of the implantable medical device housing, the ferrule including:
an exterior flange configured to abut an exterior surface of the housing, the exterior flange defining an exit opening;
a tunnel extending from the exterior flange, the tunnel defining a tunnel interior extending away from the exit opening and terminating at an inlet opening of the ferrule;
at least one interior tab extending away from an interior of the tunnel in a direction generally aligned with the exterior flange such that a first surface of the at least one interior tab faces the exterior flange and a second opposite surface of the at least one interior tab faces away from the exterior flange, the at least one interior tab configured to exert a spring bias with the first surface directly against an interior surface of the housing and toward the exterior flange while the exterior flange abuts the exterior surface of the housing to draw the exterior flange toward the exterior surface of the housing;
an electrically insulative insert disposed at least partially inside the tunnel; and
a hermetic seal disposed between the electrically insulative insert and the tunnel.

7. The system of claim 6, wherein the hermetic seal includes gold.

8. The system of claim 6, wherein a top surface of the exterior flange defines a recess encircling the exit opening.

9. The system of claim 8, wherein the hermetic seal substantially fills the recess.

10. The system of claim 6, wherein the tunnel includes a notch along its length, away from the opening, with the at least one interior tab extending away from the notch.

11. The system of claim 10, wherein the at least one interior tab is bent away from material defining the tunnel.

12. The system of claim 6, wherein the at least one interior tab is one of a plurality of interior tabs disposed around the tunnel.

13. The system of claim 6, comprising at least one conductor extending through the electrically insulative insert.

14. The system of claim 13, wherein the at least one conductor is one of a plurality of conductors, and wherein respective conductors are respectively coupled to a respective terminal of a capacitor disposed on a circuit coupled to the ferrule.

15. The system of claim 14, wherein some of the conductors are electrically coupled to a common polarity.

16. The system of claim 15, wherein housing is metallic and at least one of the plurality of conductors is in electrical communication with the housing and an opposite polarity terminal of each of the respective capacitors.

17. An implantable medical device, including:
a housing, including an interior portion, an exterior portion, and a first passage between the interior and exterior portions of the housing, the housing configured to carry and hermetically enclose an electronic circuit; and
a capacitive filter ferrule, configured to be located at least partially within the first passage between the interior and exterior portions of the housing to allow capacitively-filtered passage of an electrical connection there between, the capacitive filter ferrule including:
an electrically-conductive outer ferrule portion, configured to be located toward the exterior portion of the housing;
an inner ferrule portion, configured to be located toward the interior portion of the housing, the inner ferrule portion non-integrally formed with the outer ferrule portion but attached to the outer ferrule portion;
the electrical connection; and
a dielectric plug, electrically isolating the electrical connection from the electrically-conductive outer ferrule portion;
wherein the inner ferrule portion includes a flexing spring flange extending laterally outward in a direction generally aligned with the outer ferrule portion such that a first surface of the flexing spring flange faces the outer ferrule portion and a second, opposite surface of the flexing spring flange faces away from the outer ferrule portion and with the first surface of the flexing spring flange biasing directly against the interior portion of the housing and also extending toward and biasing against a portion of an interior wall of the housing adjacent to the first passage between the interior and exterior portions of the housing to draw the outer ferrule portion toward the exterior portion of the housing.

18. The device of claim 17,
wherein the outer ferrule portion includes a stamped sheet metal portion that is sized and shaped to accept a portion of the dielectric plug therewithin and to fit snugly at least partially within the first passage between the interior and exterior portions of the housing; and
wherein the inner ferrule portion includes a stamped sheet metal portion that is sized and shaped to accept a portion of the dielectric plug therewithin and to provide the flexing flange.

19. The device of claim 17, wherein the inner ferrule portion is electrically-conductive and includes an electrically-conductive tab extending laterally toward an interior of the first passage between the interior and exterior portions of the housing, the electrically-conductive tab including a second passage capable of passing an electrical conductor therethough so as to permit an electrical connection between the electrical conductor and the electrically-conductive tab.

* * * * *